US012054536B2

(12) United States Patent
Barria et al.

(10) Patent No.: US 12,054,536 B2
(45) Date of Patent: Aug. 6, 2024

(54) ANTIBODIES TO ANDES HANTAVIRUS, AND METHODS FOR USING SAME

(71) Applicants: Ichor Biologics, LLC, New York, NY (US); Universidad De Concepcion, Concepcion (CL)

(72) Inventors: Maria Ines Barria, Concepcion (CL); Jose Luis Garrido Ramirez, Concepcion (CL); Felipe Edgardo Bravo Caceres, Concepcion (CL)

(73) Assignees: Ichor Biologics, LLC, New York, NY (US); Universidad De Concepcion, Concepcion (CL)

( * ) Notice: Subject to any disclaimer, the term of this patent is extended or adjusted under 35 U.S.C. 154(b) by 0 days.

(21) Appl. No.: 17/742,481

(22) Filed: May 12, 2022

(65) Prior Publication Data

US 2022/0298229 A1    Sep. 22, 2022

Related U.S. Application Data

(62) Division of application No. 16/495,624, filed as application No. PCT/US2018/023483 on Mar. 21, 2018, now Pat. No. 11,359,006.

(60) Provisional application No. 62/474,681, filed on Mar. 22, 2017, provisional application No. 62/639,008, filed on Mar. 6, 2018.

(51) Int. Cl.
*C07K 16/10* (2006.01)
*A61P 31/14* (2006.01)
*A61K 39/00* (2006.01)

(52) U.S. Cl.
CPC ............. *C07K 16/10* (2013.01); *A61P 31/14* (2018.01); *A61K 2039/505* (2013.01); *C07K 2317/21* (2013.01); *C07K 2317/76* (2013.01)

(58) Field of Classification Search
None
See application file for complete search history.

(56) References Cited

U.S. PATENT DOCUMENTS

2020/0087381 A1    3/2020    Barria et al.

OTHER PUBLICATIONS

GenBank Accession# AAO11880, immunoglobulin lambda light chain variable region, partial [*Homo sapiens*]., Jul. 24, 2016.*
GenBank Accession #AAF35175, immunoglobulin heavy chain variable region, partial [*Homo sapiens*], Jul. 26, 2016.*
Garrido et al., Two recombinant human monoclonal antibodies that protect against lethal Andes hantavirus infection in vivo, 2018, Sci Transl Med, vol. 10, pp. 1-11.*
Hjelle, B. and Torres-Pérez, F., Hantaviruses in the Americas and their role as emerging pathogens. Viruses Dec. 2010;2(12):2559-86.
Martinez-Valdebenito, C., et al., Person-to-person household and nosocomial transmission of Andes hantavirus, Southern Chile, 2011. Emerg. Infect. Dis. 2014;20(10):1629-36.
Martinez, V.P., et al., Person-to-person transmission of Andes virus. Emerg. Infect. Dis. 2005;11(12):1848-53.
Padula, P.J., et al., Hantavirus pulmonary syndrome outbreak in Argentina: molecular evidence for person-to-person transmission of Andes virus. Virology 1998; 241 (2):323-30.
Wells, R.M., et al., Hantavirus transmission in the United States. Emerg. Infect. Dis. 1997; 3: 361-5.
Vaheri, A., et al., Uncovering the mysteries of hantavirus infections. Nat. Rev. Microbiol. 2013; 11(8):539-50.
Padula, P., et al., Transmission study of Andes hantavirus infection in wild sigmodontine rodents. J. Virol. 2004; 78:11972-9.
Schountz, T. and Prescott, J., Hantavirus Immunology of Rodent Reservoirs: Current Status and Future Directions. Viruses 2014; 6(3):1317-1335.
Vial, P.A., et al., Incubation period of hantavirus cardiopulmonary syndrome. Emerg. Infect. Dis. 2006; 12:1271-3.
Mertz, G.J., et al., Diagnosis and treatment of new world hantavirus infections. Curr. Opin. Infect. Dis. 2006; 19 (5):437-42.
Vial, P.A., et al., Hantavirus Study Group in Chile. High-dose intravenous methylprednisolone for hantavirus cardiopulmonary syndrome in Chile: a double-blind, randomized controlled clinical trial. Clin. Infect. Dis. Oct. 2013; 57 (7):943-51.
MacNeil, A., et al., Sin Nombre virus-specific immunoglobulin M and G kinetics in hantavirus pulmonary syndrome and the role played by serologic responses in predicting disease outcome. J. Infect. Dis. 2010; 202:242-6.
Bharadwaj, M., et al., Humoral immune responses in the hantavirus cardiopulmonary syndrome. J. Infect. Dis. 2000; 182(1):43-8.
Ye, C., et al., Neutralizing antibodies and Sin Nombre virus RNA after recovery from hantavirus cardiopulmonary syndrome. Emerg. Infect. Dis. 2004; 10(3):478-82.
Custer, D.M., et al., Active and passive vaccination against hantavirus pulmonary syndrome with Andes virus M genome segment-based DNA vaccine. J. Virol. 2003; 77(18): 9894-905.
Hooper, J.W., et al., Immune serum produced by DNA vaccination protects hamsters against lethal respiratory challenge with Andes virus. J. Virol. 2008; 82(3):1332-8.
Brocato, R., et al., DNA vaccine-generated duck polyclonal antibodies as a postexposure prophylactic to prevent hantavirus pulmonary syndrome (HPS). PLoS One 2012; 7:e35996.
Hooper, J.W., et al., DNA vaccine-derived human IgG produced in transchromosomal bovines protect in lethal models of hantavirus pulmonary syndrome. Sci. Transl. Med. 2014; 6(264):264ra162.

(Continued)

*Primary Examiner* — Benjamin P Blumel

(74) *Attorney, Agent, or Firm* — Alan J. Morrison

(57) ABSTRACT

This invention provides isolated human antibodies and recombinant proteins comprising defined heavy chains and light chains, wherein the antibodies and recombinant proteins neutralize Andes Virus with defined IC50 values. This invention also provides related pharmaceutical compositions, treatment methods and kits.

21 Claims, 19 Drawing Sheets

Specification includes a Sequence Listing.

(56) References Cited

OTHER PUBLICATIONS

Haese, N., et al., Antiviral Biologic Produced in DNA Vaccine/Goose Platform Protects Hamsters Against Hantavirus Pulmonary Syndrome When Administered Post-exposure. PLoS Negl. Trop. Dis. 2015; 9(6):e0003803.

Vial, P.A., et al., Hantavirus Study Group in Chile. A non-randomized multicentre trial of human immune plasma for treatment of hantavirus cardiopulmonary syndrome caused by Andes virus. Antivir. Ther. 2015; 20(4):377-86.

Dolgin, E., Hantavirus treatments advance amidst outbreak in US park. Nat. Med. 2012; 18(10):1448.

Enria, D.A., et al., Importance of dose of neutralising antibodies in treatment of Argentine haemorrhagic fever with immune plasma. Lancet 1984; 2(8397):255-6.

Casadevall, A., et al., Passive antibody therapy for infectious diseases. Nat. Rev. Microbiol. 2004; 2(9):695-703.

Wilson, P.C. and Andrews, S.F., Tools to therapeutically harness the human antibody response. Nat. Rev. Immunol. 2012; 12:709-19.

Scheid, J.F., et al., Broad diversity of neutralizing antibodies isolated from memory B cells in HIV-infected individuals. Nature 2009; 458:636-40.

Mouquet, H., et al., Memory B cell antibodies to HIV-1 gp140 cloned from individuals infected with clade A and B viruses. PLoS One 2011; 6:e24078.

Wu, X., et al., Rational design of envelope identifies broadly neutralizing human monoclonal antibodies to HIV-1. Science 2010; 329:856-61.

Tiller, T., et al., Efficient generation of monoclonal antibodies from single human B cells by single cell RT-PCR and expression vector cloning. J. Immunol. Methods 2008; 329(1-2):112-24.

Smith, K., et al., Rapid generation of fully human monoclonal antibodies specific to a vaccinating antigen. Nat. Protoc. 2009; 4(3):372-84.

Dunbar, J., and Deane, C.M., ANARCI: antigen receptor numbering and receptor classification, Bioinformatics, vol. 32, Issue 2, Jan. 15, 2016, pp. 298-300, https://doi.org/10.1093/bioinformatics/btv552.

Abhinandan, K.R., and Martin, A.C.R., Analysis and improvements to Kabat and structurally correct numbering of antibody variable domains. 2008 Mol. Immunol., 45:3832-3839.

Geuijen, C.A., et al., Affinity ranking of antibodies using flow cytometry: application in antibody phage display-based target discovery. Journal of Immunological Methods 2005; (302):68-77.

Yu, L., et al., A recombinant pseudotyped lentivirus expressing the envelope glycoprotein of hantaan virus induced protective immunity in mice. Virol. J. Oct. 5, 2013; 10:301.

Hooper, J.W., et al., A lethal disease model for hantavirus pulmonary syndrome. Virol. 2001; (289):6-14.

Martinez, V.P. and Padula, P.J., Induction of protective immunity in a Syrian hamster model against a cytopathogenic strain of Andes virus. J. Med. Virol. 2012; (84):87-95.

Safronetz, D., et al., Pathogenesis and host response in Syrian hamster following intranasal infection with Andes virus. PLoS Pathog., Dec. 2011; 7(12):e1002426.

Howell, K.A., et al., Antibody Treatment of Ebola and Sudan Virus Infection via a Uniquely Exposed Epitope within the Glycoprotein Receptor-Binding Site. Cell Rep. 2016; 17;15(7):1514-26.

Corti, D., et al., Protective monotherapy against lethal Ebola virus infection by a potently neutralizing antibody. Science. 2016; 18;351(6279):1339-42.

Prescott, J., et al., Postmortem stability of Ebola virus, Emerg. Infect. Dis. May 2015; 21(5):856-9.

Marasco, W.A. and Sui, J., The growth and potential of human antiviral monoclonal antibody therapeutics, Nat. Biotechnol. Dec. 2007; 25(12):1421-34.

\* cited by examiner

```
AGAGGTGCAGCTGGTGCAGTCTGGGGCTGAACTAAAAAAGCCTGGGTCTTCGGTCAAGGT
 E   V   Q   L   V   Q   S   G   A   E   L   K   K   P   G   S   S   V   K   V

CTCCTGCAAGGCTTCCGGAGGCACCTTCGTCGGCTATGGTGTCAGCTGGGTGCGACAGGT
 S   C   K   A   S   G   G   T   F  |V   G   Y   G   V   S| W   V   R   Q   V

CCCCGGACATGGACCTGAGTGGATGGGAGGATTCAGCCCTATCTCCAATACTGCAAACTA
 P   G   H   G   P   E  |W   M   G   G   F   S   P   I   S   N   T   A   N| Y

TGCAGAGAGGTTCCAGGGCAGAGTCACCATGATCGTGGACGGATCCACGAGCACAGCCTA
 A   E   R   F   Q   G   R   V   T   M   I   V   D   G   S   T   S   T   A   Y

CATGGAACTGCGAAGCCTGAGATCTGAGGACACGGCCATATATTATTGTGCGAGATCTTG
 M   E   L   R   S   L   R   S   E   D   T   A   I   Y   Y   C  |A   R   S   C

CGACTTCTGGAATGCCTATTACAACAATTGGTTCGACCCTGGGGCCAGGGAACCCTGGT
 D   F   W   N   A   Y   Y   N   N   W   F   D| P   W   G   Q   G   T   L   V

CACTGTCTCCTCA
 T   V   S   S
```

Figure 1A

```
TCCTGGGCCCAGTCTGCCCTGACTCAGCCTGCCTCCGTGTCTGGGTCTCCTGGACAGTCG
 S  W  A  Q  S  A  L  T  Q  P  A  S  V  S  G  S  P  G  Q  S

ATCACCATCTCCTGCACTGGGACCAGCAGTGAC TTTGCTGATTATAATTCTGTCTCTTGG
 I  T  I  S  C  T  G  T  S  S  D  F  A  D  Y  N  S  V  S  W

TAC CAACAACACCCAGGCAAAGCCCCCAAA CTCCTGATTTTTGATGTCAATGATCGGCCC
 Y  Q  Q  H  P  G  K  A  P  K  L  L  I  F  D  V  N  D  R  P

TCAGGGGTTTCTCATCGCTTCTCTGGCTCCAAGTCTGGCAACACGGCCTCCCTGACCATC
 S  G  V  S  H  R  F  S  G  S  K  S  G  N  T  A  S  L  T  I

TCTGGGCTCCAGGCTGAAGACGAGTCTGACTATTACTGC ACCTCATATACCATCTGCAAT
 S  G  L  Q  A  E  D  E  S  D  Y  Y  C  T  S  Y  T  I  C  N

TCTTAT GTCTTCGGGACTGGGACCAAGGTCACCGTCCTAGGTCAGCCCAAGGCCAACCCC
 S  Y  V  F  G  T  G  T  K  V  T  V  L  G  Q  P  K  A  N  P

ACTGTCCCTCTGTTCCCACC
 T  V  P  L  F  P
```

Figure 1B

| Ab | Chain | Family | Top V gene match | Top D gene match | Top J gene match | Chain type |
|---|---|---|---|---|---|---|
| MIB22 | Heavy | vh1-69 | IGHV1-69*13,IGHV1-69*01,IGHV1-69D*01 | IGHD3-10*02,IGHD1-7*01,IGHD3-3*01 | IGLJ5*02 | VH |
| MIB22 | Lambda | IGLV2-14 | IGLV2-14*03 | | IGLJ1*01 | VL |

Figure 1C

```
ACAGGTGCAGCTGCAGGAGTCGGGGGGAGGCTTAGTTCAGCCTGGGGGGTCCCTGAGACT
 Q   V   Q   L   Q   E   S   G   G   G   L   V   Q   P   G   G   S   L   R   L

CTCCTGTGCAGCCTCTGGAGTCACCTT|AGCAGATACTGGATGCAC|GGGTCCGCCAAGC
 S   C   A   A   S   G   V   T   F | S   R   Y   W   M   H | W   V   R   Q   A

TCCAGGAAAGGGGCTGGT|TGGGTCGCTGGTGTTAATAGTGATGGGAGTAGCAGAACG|TA
 P   G   K   G   L   V | W   V   A   G   V   N   S   D   G   S   S   R   T | Y

CGCGGACTCTGTGAAGGGCCGACTCACCATCTCCAGAGACAACGCCAAGAATACGGTGTC
 A   D   S   V   K   G   R   L   T   I   S   R   D   N   A   K   N   T   V   S

TCTACAAATGGAAAGTCTGAGAGTCGACGACACGGCTCTATATTTTTGT|GTGAGCGGCAT
 L   Q   M   E   S   L   R   V   D   D   T   A   L   Y   F   C | V   S   G   M

|GACGGTTTTTGGAATGATCAGGCCTCAGGTTTTTCATGTG|TGGGGCCAAGGGACAATGGT
 T   V   F   G   M   I   R   P   Q   V   F   H   V | W   G   Q   G   T   M   V

CACCGTCTCTTCA
 T   V   S   S
```

Figure 2A

```
TCCTGGGCCCAGTCTGTGCTGACTCAGAAGCCCTCAGTCTCTGGGGCCCCAGGGCAGAGC
 S   W   A   Q   S   V   L   T   Q   P   P   S   V   S   G   A   P   G   Q   S

GTCACCATCTCCTGCACTGGAACCAGCTCCAACATCGGGGCAGGTTATGATGTACACTGG
 V   T   I   S   C   T   G   T   S   S   N   I   G   A   G   Y   D   V   H   W

TACCAGCAACTTGCAGGAACAGCCCCCAAACTCCTCATCTATGTTAACAGCGATCGGCCC
 Y   Q   Q   L   A   G   T   A   P   K   L   L   I   Y   V   N   S   D   R   P

TCAGGGGTCCCTGACCGATTCTCTGGCTCCAAGTCTGGCACCTCAGCCTCCCTGGCCATC
 S   G   V   P   D   R   F   S   G   S   K   S   G   T   S   A   S   L   A   I

ACTGGCTCCAGGCTGAGGACGAGGGTGACTATTACTGCCAGTCCTATGACAGCAGCCTG
 T   G   L   Q   A   E   D   E   G   D   Y   Y   C   Q   S   Y   D   S   S   L

AGTGCTGTCGTATTCGGCGGAGGGACCAAGTTGACCGTCCTACGTCAGCCCAAGGCTGCC
 S   A   V   V   F   G   G   G   T   K   L   T   V   L   R   Q   P   K   A   A

CCCTCGGTCACTCTGTTCCCACC
 P   S   V   T   L   F   P   P
```

Figure 2B

| Ab | Chain | Family | Top V gene match | Top D gene match | Top J gene match | Chain type |
|---|---|---|---|---|---|---|
| JL16 | Heavy | IGHV3-74 | IGHV3-74*03 | IGHD3-3*02,IGHD3-3*01 | IGHJ3*02 | VH |
| JL16 | Lambda | IGLV1-40 | IGLV1-40*01,IGLV1-40*02 | | IGLJ2*01,IGLJ3*01 | VL |

Hanta negative IgG

Anti-ANDV mAb MIB22

Figure 4E

GPC ANDV pseudovirus

- Isotype cont
- MIB22 Ab
- JL16 Ab
- Total IgG P1

Y-axis: % Neutralization
X-axis: $\text{Log}_{10}$ (ug antibody/ml)

Figure 6A

SEQUENCE LISTING

```
<160> NUMBER OF SEQ ID NOS: 20

<210> SEQ ID NO 1
<211> LENGTH: 373
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
agaggtgcag ctggtgcagt ctggggctga actaaaaaag cctgggtctt cggtcaaggt      60
ctcctgcaag gcttccggag gcaccttcgt cggctatggt gtcagctggg tgcgacaggt     120
ccccggacat ggacctgagt ggatgggagg attcagccct atctccaata ctgcaaacta     180
tgcagagagg ttccagggca gagtcacgat gatcgtggac ggatccacga gcacagccta     240
catggaactg cgaagcctga gatctgagga cacggccata tattattgtg cgagatcttg     300
cgacttctgg aatgcctatt acaacaattg gttcgacccc tggggccagg gaaccctggt     360
cactgtctcc tca                                                        373

<210> SEQ ID NO 2
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2
```

Glu Val Gln Leu Val Gln Ser Gly Ala Glu Leu Lys Lys Pro Gly Ser
1               5                   10                  15

Ser Val Lys Val Ser Cys Lys Ala Ser Gly Gly Thr Phe Val Gly Tyr
            20                  25                  30

Gly Val Ser Trp Val Arg Gln Val Pro Gly His Gly Pro Glu Trp Met
        35                  40                  45

Gly Gly Phe Ser Pro Ile Ser Asn Thr Ala Asn Tyr Ala Glu Arg Phe
    50                  55                  60

Gln Gly Arg Val Thr Met Ile Val Asp Gly Ser Thr Ser Thr Ala Tyr
65                  70                  75                  80

Met Glu Leu Arg Ser Leu Arg Ser Glu Asp Thr Ala Ile Tyr Tyr Cys
                85                  90                  95

Ala Arg Ser Cys Asp Phe Trp Asn Ala Tyr Tyr Asn Asn Trp Phe Asp
            100                 105                 110

Pro Trp Gly Gln Gly Thr Leu Val Thr Val Ser Ser
        115                 120

<210> SEQ ID NO 3
<211> LENGTH: 380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
tcctgggccc agtctgccct gactcagcct gcctccgtgt ctgggtctcc tggacagtcg      60
atcaccatct cctgcactgg gaccagcagt gactttgctg attataattc tgtctcttgg     120
taccaacaac acccaggcaa agcccccaaa ctcctgattt ttgatgtcaa tgatcggccc     180 tcagggggttt ctcatcgctt ctctggctcc aagtctggca acacggcctc cctgaccatc     240
tctgggctcc aggctgaaga cgagtctgac tattactgca cctcatatac catctgcaat     300
tcttatgtct tcgggactgg gaccaaggtc accgtcctag gtcagcccaa ggccaacccc     360
actgtccctc tgttcccacc                                                  380

<210> SEQ ID NO 4
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ser Trp Ala Gln Ser Ala Leu Thr Gln Pro Ala Ser Val Ser Gly Ser
1               5                   10                  15

Pro Gly Gln Ser Ile Thr Ile Ser Cys Thr Gly Thr Ser Ser Asp Phe
            20                  25                  30

Ala Asp Tyr Asn Ser Val Ser Trp Tyr Gln Gln His Pro Gly Lys Ala
        35                  40                  45

Pro Lys Leu Leu Ile Phe Asp Val Asn Asp Arg Pro Ser Gly Val Ser
    50                  55                  60

His Arg Phe Ser Gly Ser Lys Ser Gly Asn Thr Ala Ser Leu Thr Ile
65                  70                  75                  80

Ser Gly Leu Gln Ala Glu Asp Glu Ser Asp Tyr Tyr Cys Thr Ser Tyr
                85                  90                  95

Thr Ile Cys Asn Ser Tyr Val Phe Gly Thr Gly Thr Lys Val Thr Val

```
                        100                 105                 110
Leu Gly Gln Pro Lys Ala Asn Pro Thr Val Pro Leu Phe Pro Pro
        115                 120                 125

<210> SEQ ID NO 5
<211> LENGTH: 373
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
acaggtgcag ctgcaggagt cggggggagg cttagttcag cctgggggt  ccctgagact    60 ctcctgtgca gcctctggag tcaccttcag cagatactgg atgcactggg tccgccaagc   120
tccaggaaag gggctggtgt gggtcgctgg tgttaatagt gatgggagta gcagaacgta   180
cgcggactct gtgaagggcc gactcaccat ctccagagac aacgccaaga atacggtgtc   240
tctacaaatg gaaagtctga gagtcgacga cacggctcta tattttgtgt gagcggcat    300 gacggttttt ggaatgatca ggcctcaggt ttttcatgtg tggggccaag gacaatggt    360 caccgtctct tca                                                       373

<210> SEQ ID NO 6
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Gln Glu Ser Gly Gly Gly Leu Val Gln Pro Gly Gly
1               5                   10                  15

Ser Leu Arg Leu Ser Cys Ala Ala Ser Gly Val Thr Phe Ser Arg Tyr
            20                  25                  30

Trp Met His Trp Val Arg Gln Ala Pro Gly Lys Gly Leu Val Trp Val
        35                  40                  45

Ala Gly Val Asn Ser Asp Gly Ser Ser Arg Thr Tyr Ala Asp Ser Val
    50                  55                  60

Lys Gly Arg Leu Thr Ile Ser Arg Asp Asn Ala Lys Asn Thr Val Ser
65                  70                  75                  80

Leu Gln Met Glu Ser Leu Arg Val Asp Asp Thr Ala Leu Tyr Phe Cys
                85                  90                  95

Val Ser Gly Met Thr Val Phe Gly Met Ile Arg Pro Gln Val Phe His
            100                 105                 110

Val Trp Gly Gln Gly Thr Met Val Thr Val Ser Ser
        115                 120

<210> SEQ ID NO 7
<211> LENGTH: 383
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
tcctgggccc agtctgtgct gactcagccg ccctcagtct ctggggcccc agggcagagc    60
gtcaccatct cctgcactgg aaccagctcc aacatcgggg caggttatga tgtacactgg   120
```

```
taccagcaac ttgcaggaac agcccccaaa ctcctcatct atgttaacag cgatcggccc    180 tcagggtcc ctgaccgatt ctctggctcc aagtctggca cctcagcctc cctggccatc    240
actgggctcc aggctgagga cgagggtgac tattactgcc agtcctatga cagcagcctg    300
agtgctgtcg tattcggcgg agggaccaag ttgaccgtcc tacgtcagcc caaggctgcc    360
ccctcggtca ctctgttccc acc                                            383
```

```
<210> SEQ ID NO 8
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ser Trp Ala Gln Ser Val Leu Thr Gln Pro Pro Ser Val Ser Gly Ala
1               5                   10                  15

Pro Gly Gln Ser Val Thr Ile Ser Cys Thr Gly Thr Ser Ser Asn Ile
            20                  25                  30

Gly Ala Gly Tyr Asp Val His Trp Tyr Gln Gln Leu Ala Gly Thr Ala
        35                  40                  45

Pro Lys Leu Leu Ile Tyr Val Asn Ser Asp Arg Pro Ser Gly Val Pro
    50                  55                  60

Asp Arg Phe Ser Gly Ser Lys Ser Gly Thr Ser Ala Ser Leu Ala Ile
65                  70                  75                  80

Thr Gly Leu Gln Ala Glu Asp Glu Gly Asp Tyr Tyr Cys Gln Ser Tyr
                85                  90                  95

Asp Ser Ser Leu Ser Ala Val Val Phe Gly Gly Gly Thr Lys Leu Thr
            100                 105                 110

Val Leu Arg Gln Pro Lys Ala Ala Pro Ser Val Thr Leu Phe Pro Pro
        115                 120                 125

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtcggctatg gtgtcagc                                                   18

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tggatgggag gattcagccc tatctccaat actgcaaac                            39

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 11
gcgagatctt gcgacttctg gaatgcctat tacaacaatt ggttcgac                48

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tttgctgatt ataattctgt ctcttggtac                                    30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctcctgattt ttgatgtcaa tgatcggccc                                    30

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
acctcatata ccatctgcaa ttcttat                                       27

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agcagatact ggatgcac                                                 18

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgggtcgctg gtgttaatag tgatgggagt agcaga                             36

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 17
gagcggcatg acggtttttg gaatgatcag gcctcaggtt tttcat                46

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
atcggggcag gttatgatgt acactgg                                     27

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ctcctcatct atgttaacag cgatcggccc                                  30

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cagtcctatg acagcagcct gagtgctgtc gta                              33
```

ANTIBODIES TO ANDES HANTAVIRUS, AND METHODS FOR USING SAME

This application is a divisional of U.S. Ser. No. 16/495,624, filed Sep. 19, 2019, which is a § 371 national stage entry of PCT Application No. PCT/US2018/023483, filed Mar. 21, 2018, which claims the benefit of U.S. Provisional Applications No. 62/474,681, filed Mar. 22, 2017, and 62/639,008, filed Mar. 6, 2018, the contents of all of which are incorporated herein by reference.

Throughout this application, various publications are cited. The disclosure of these publications is hereby incorporated by reference into this application to describe more fully the state of the art to which this invention pertains.

BACKGROUND OF THE INVENTION

Hantavirus cardiopulmonary syndrome (HCPS) is a severe disease that causes a thirty-five to forty percent mortality rate in people infected with either of two closely related new world hantaviruses. In North America, HCPS is caused by Sin Nombre Virus (SNV). In South America, it is caused by Andes Virus (ANDV). The major mode of hantavirus transmission occurs when humans come into close contact with aerosols derived from the urine, feces or saliva of infected animals (1). In particular, ANDV poses a unique threat, since unlike other hantaviruses, ANDV has been shown to have the capacity to spread human-to-human (2-5). In Chile alone, more than 904 cases of HCPS have been reported during the period 1995-2014 (6). Considering that ANDV infection has no effective cure, treatment, or vaccine, this emerging pathogen must be considered a major threat to global public health.

Hantaviruses are negative-sense single-stranded RNA viruses belonging to the bundyaviridae family of viruses. These viruses contain a tri-segmented genome that encodes for a nucleocapsid protein (N), two viral glycoproteins (Gn and Gc), and a viral RNA polymerase (RdRp) (7). The natural hosts for these viruses are rodents (e.g., mice, moles and voles), insectivores and bats. However, transmission to humans most commonly occurs via rodent-to-human transmission (6-8). Notably in rodent reservoirs, infection persists in spite of the evolution of neutralizing host immune responses against the virus (9). Interestingly, infection in rodents is predominantly asymptomatic, while in humans, infection is characterized by severe pathology.

In humans, HCPS is characterized by fever, headache and gastrointestinal symptoms anywhere from 7-14 days post-aerosol exposure to hantavirus (10). This is followed by a 2-7-day period characterized by falling blood pressure, lung edema, cardiac shock and death in a significant number of patients (11). While no curative treatment exists, studies have examined the potential of methylprednisolone to treat HCPS (12). In one study, 60 patients presenting with moderate to severe HCPS were treated with methylprednisolone. However, no beneficial effect on disease severity, viral load or mortality was observed (12).

Despite these setbacks, there is potential for a treatment, since there are several lines of evidence indicating that neutralizing antibodies can control HCPS in-vivo. In HCPS patients, high hantavirus-specific IgG levels early in disease have been associated with survival (13). In addition, high titers of neutralizing antibodies correlate with milder disease outcomes and faster recovery (14-15). Furthermore, in small animal models, the passive transfusion of hantavirus-specific antibodies protected animals from ANDV infection and HPCS (16-20).

These lines of evidence provided a rationale for treating acute HCPS with the passive transfusion of plasma from ANDV-convalescent patients (21, 22). The plasma used in that study originated from patients that had resolved ANDV infection, and whose plasma possessed high titers of ANDV-neutralizing antibodies (23). That trial demonstrated that treatment with ANDV-convalescent plasma led to a significant reduction in symptoms and fatalities (21, 22). Mortalities were reduced to 14% (4 of 29 patients) in centers treating patients with convalescent plasma, as compared to 32% (63 of 199 patients) in medical centers not participating in that study during the same period.

While these data support the concept that the passive administration of convalescent serum might treat HCPS patients, several limitations exist in pursuing that line of treatment. The passive infusion of human plasma runs the risk of blood-borne pathogen transmission. Additionally, there is a high cost of production, as well as difficulties in standardizing dose and inconsistent efficiencies across donor plasma samples (24).

To circumvent these issues, ANDV-specific monoclonal IgG with the capacity to neutralize infection could be explored as an alternative to polyclonal convalescent patient plasma. Since most convalescent patients possess high titers of neutralizing antibodies directed against viral glycoproteins, they represent the ideal B cell donors for developing therapeutic monoclonal antibodies.

The latest technology for producing antigen-specific monoclonal antibodies (mAbs) from human B cells has allowed a rapid increase in the isolation and characterization of human monoclonal antibody (25). Indeed, several recent studies have successfully used antigen-baiting as a technique to obtain specific human monoclonal antibodies against viruses from IgG+ memory B cell pools from infected donors (26-28). The antigen-specific variable regions of these antibodies are used to generate novel recombinant IgG against selected pathogens. This method monoclonal antibody development allows for the selection of pathogen-specific antibodies that recognize exposed epitopes on higher order structures on physiologically relevant antigens (25).

Despite these antibody-related advances, there exists an unmet need for monoclonal antibodies having sufficiently high ANDV-neutralizing capacity while also having sufficiently low IC50 values.

SUMMARY OF THE INVENTION

This invention provides a first isolated human antibody comprising two heavy chains and two light chains, (i) wherein each heavy chain comprises a variable region having the amino acid sequence shown in FIG. 1A, and each light chain comprises a variable region having the amino acid sequence shown in FIG. 1B, and (ii) wherein the antibody neutralizes Andes Virus with an IC50 of below 2.0 µg/ml. This invention also provides a first recombinant protein comprising an Andes Virus-binding domain that comprises two polypeptide regions, (i) wherein the first region has the amino acid sequence shown in FIG. 1A, and the second region has the amino acid sequence shown in FIG. 1B, and (ii) wherein the protein neutralizes Andes Virus with an IC50 of below 2.0 µg/ml. This invention also provides a first composition comprising (i) the first antibody or the first recombinant protein, and (ii) a pharmaceutically acceptable carrier.

This invention provides a method for reducing the likelihood of a human subject's becoming symptomatic of an Andes Virus infection, wherein the subject is at risk of becoming exposed to Andes Virus, the method comprising administering to the subject an effective amount of the first composition. This invention also provides a method for reducing the likelihood of a human subject's becoming symptomatic of an Andes Virus infection, wherein the subject has or may have recently been exposed to Andes Virus, the method comprising administering to the subject an effective amount of the first composition. This invention further provides a method for treating a human subject who is infected with Andes Virus and symptomatic of that infection, the method comprising administering to the subject an effective amount of the first composition.

This invention still further provides a kit comprising, in separate compartments, (i) a dry component of a pharmaceutically acceptable carrier admixed with the first antibody and/or with the first recombinant protein, and (ii) a liquid component of a pharmaceutically acceptable carrier.

This invention provides a second isolated human antibody comprising two heavy chains and two light chains, (i) wherein each heavy chain comprises a variable region having the amino acid sequence shown in FIG. 2A, and each light chain comprises a variable region having the amino acid sequence shown in FIG. 2B, and (ii) wherein the antibody neutralizes Andes Virus with an IC50 of below 10.0 µg/ml. This invention also provides a second recombinant protein comprising an Andes Virus-binding domain that comprises two polypeptide regions, (i) wherein the first region has the amino acid sequence shown in FIG. 2A, and the second region has the amino acid sequence shown in FIG. 2B, and (ii) wherein the protein neutralizes Andes Virus with an IC50 of below 10.0 µg/ml. This invention also provides a second composition comprising (i) the second antibody or the second recombinant protein, and (ii) a pharmaceutically acceptable carrier.

This invention provides a method for reducing the likelihood of a human subject's becoming symptomatic of an Andes Virus infection, wherein the subject is at risk of becoming exposed to Andes Virus, the method comprising administering to the subject an effective amount of the second composition. This invention also provides a method for reducing the likelihood of a human subject's becoming symptomatic of an Andes Virus infection, wherein the subject has or may have recently been exposed to Andes Virus, the method comprising administering to the subject an effective amount of the second composition. This invention further provides a method for treating a human subject who is infected with Andes Virus and symptomatic of that infection, the method comprising administering to the subject an effective amount of the second composition.

Finally, this invention provides a kit comprising, in separate compartments, (i) a dry component of a pharmaceutically acceptable carrier admixed with the second antibody and/or with the second recombinant protein, and (ii) a liquid component of a pharmaceutically acceptable carrier.

BRIEF DESCRIPTION OF THE FIGURES

FIGS. 1A, 1B and 1C

These figures show MIB22 heavy and light chain CDR sequences. FIG. 1A displays the heavy chain CDR amino acid and nucleotide sequences of ANDV-specific antibody MIB22. FIG. 1B displays the light chain CDR amino acid and nucleotide sequences of ANDV-specific antibody MIB22. CDR sequences are highlighted in yellow boxes. FIG. 1C shows the V(D)J composition of the variable antibody domains and the complementarity-determining regions that were determined using the ANARCI: antigen receptor numbering and receptor classification software. FIG. 1A: heavy chain 373 nt; CDR1=GTCGGCTATGGTGTCAGC (SEQ ID NO: 9); CDR2=TGGATGGGAGGATTCAGCCCTATC TCCAATACTGCAAAC (SEQ ID NO: 10); and CDR3=GCGAGATCTTGCGACTTCTGGAATG CCTATTACAACAATT-GGTTCGAC (SEQ ID NO: 11). FIG. 1B: lambda light chain 380 nt; CDR1=TTTGCTGATTATAATTCTGTCT CTTGGTAC (SEQ ID NO: 12); CDR2=CTCCTGATTTTTGATGTCAATGATCGGCCC (SEQ ID NO: 13); and CDR3=ACCTCATATACC ATCTGCAATTCTTAT (SEQ ID NO: 14).

FIGS. 2A, 2B and 2C

These figures show JL16 heavy and light chain CDR sequences. FIG. 2A displays the heavy chain CDR amino acid and nucleotide sequences of ANDV-specific antibody JL16. FIG. 2B displays the light chain CDR amino acid and nucleotide sequences of ANDV-specific antibody JL16. CDR sequences are highlighted in yellow boxes. FIG. 2C shows the V(D)J composition of the variable antibody domains and the complementarity-determining regions that were determined using the ANARCI: antigen receptor numbering and receptor classification software. FIG. 2A: heavy chain 373 nt; CDR1=AGCAGATACTGGATGCAC (SEQ ID NO: 15); CDR2=TGGGTCGCTGGTGTTAATA GTGATGGGAGTAGCAGA (SEQ ID NO: 16); and CDR3=GAGCGGCATGACGGTTTTTGGAAT GATCAGGCCTCAGGTT-TTTCAT (SEQ ID NO: 17). FIG. 2B: lambda light chain 380 nt; CDR1=ATCGGGGCAGGTTATGATGTACACTGG (SEQ ID NO: 18); CDR2=CTCCTCATCTATGTTAACAGC GATCGGCCC (SEQ ID NO: 19); and CDR3=CAGTCCTATGACAGCAGCC TGAGTGCTGTCGTA (SEQ ID NO: 20).

These figures show the production of ANDV-specific antibodies. 293T cells were co-transfected with 7 ug of heavy and light chain expression constructs for MIB22 and JL16, which produced the ANDV-specific monoclonal antibodies MIB22 and JL16. Supernatants were harvested 72 hours after transfection and the antibody yield was measured using a spectrophotometer at wavelength 560 nm. FIG. 3A displays the monoclonal antibody yields from three independent experiments. In FIG. 3B, IgG were purified from supernatants using A/G sepharose columns and run on a 10% SDS PAGE denaturing gel. Gels show the heavy and light chains for both MIB22 and JL16 antibodies.

FIGS. 4A, 4B, 4C, 4D and 4E

These figures show antibody binding by flow cytometry and immunofluorescence. 293T cells were transfected with an ANDV glycoprotein (GPC) expression construct. Forty-eight hours post-transfection, cells were treated with dissociation media and incubated with either (FIG. 4A) 1 µg/ml of purified IgG from a control healthy donor or an ANDV-convalescent patient (Patient #10, or "P10"); or (FIG. 4B) 1 µg/ml of monoclonal antibody JL16 or MIB22. After incubation with primary human antibody, secondary staining was conducted with an Alexa fluor 488 anti-human total IgG antibody at 4° C. Samples were analyzed by flow cytometry. In FIG. 4C, ANDV-GPC-transfected 293T cells, mock transfected 293T cells and VSV-G transfected 293T cells were incubated with 1 µg/ml to 15 µg/ml of purified IgG from P10, from a healthy donor (C4) or monoclonal antibody JL16 or MIB22. After incubation with primary human antibody, secondary staining was conducted with an Alexa fluor 488 anti-human total IgG antibody at 4° C. Samples were analyzed by flow cytometry. In FIG. 4D, the relative affinity of monoclonal antibodies were determined using ANDV-GPC-293T cells incubated with 10 μg/ml of purified polyclonal IgG from a control donor (C4), ANDV convalescent patient (P10); or monoclonal antibodies JL16 or MIB22 at 4° C. to detect monoclonal antibody off-rates. Primary IgG was then detected using an Alexa Fluor 488 anti-human IgG antibody and quantified by flow cytometry. In FIG. 4E, ANDV-GPC-transfected 293T cells were incubated with primary antibodies at a concentration of 1 μg/ml. After primary antibody incubation, cells were stained with a secondary antibody (anti-human conjugated with Alexa fluor 488). To visualize all of the cells, DAPI nuclear staining dye was used and cells were visualized using confocal microscopy.

Plasmids encoding the heavy and light chains of MIB22 have been deposited with the American Type Culture Collection (ATCC), 10801 University Boulevard, Manassas, Virginia 20110, U.S.A. Specifically, plasmids having ATCC Deposit No. PTA-127727-8 encoding the heavy and light chains of MIB22 were deposited with the ATCC on Feb. 12, 2024, under the terms of the Budapest Treaty and all restrictions imposed by the depositor on the availability to the public of the deposited material will be irrevocably removed upon the granting of the patent.

FIG. 5

This figure shows neutralization of ANDV infection using pseudotyped viral particles. 293-IB3 cells were plated in 96-well plate (8,000 cells/well) and infected with a standardized dose of ANDV (ANDV-GPC) or VSV-G (VSV-G) pseudoviral particles (9.25 ng/ml of pseudoviral particles) pre-incubated with several dilutions of sera (1/50 to 1/20000) from P10. This figure shows representative dot plots of the neutralization curves. As a control, we used cells without sera treatment or pseudoviral particles ((-) control) and cells with ANDV pseudoviral particles ((-) sera).

Figure 6B:
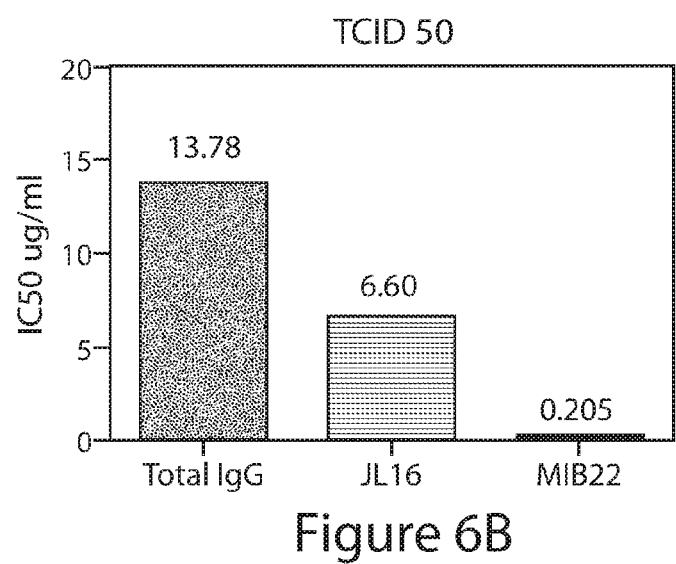

FIGS. 6A and 6B

These figures show neutralization of ANDV infection using novel monoclonal antibodies. 293-IB3 cells were plated in 96-well plate (8,000 cells/well) and infected with a standardized dose of ANDV pseudoviral particles (9.25 ng/ml of pseudoviral particles) in the presence of a titration of purified total IgG (from 0.1 □g/ml to 500 □g/ml) of P10, monoclonal antibody MIB22 and monoclonal antibody JL16. FIG. 6A displays the percent neutralization as a measure of IgG concentrations. FIG. 6B displays the average IC50 as calculated from neutralization curves from an experiment performed in quadruplicate.

Figure 7A:
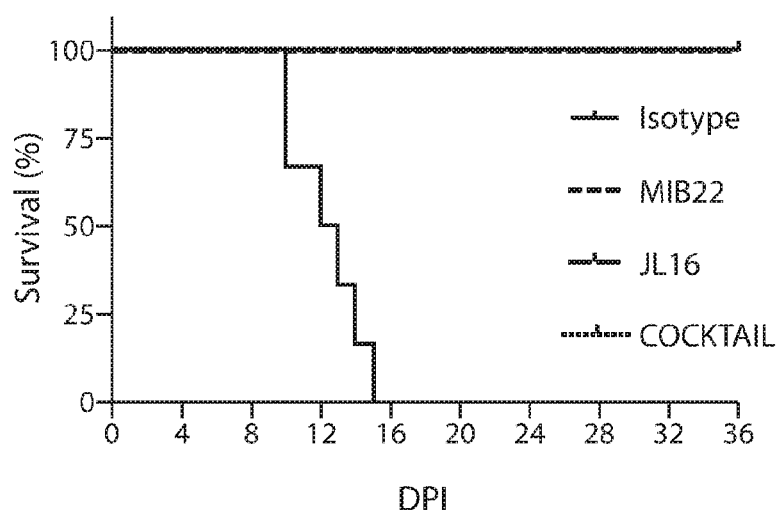
Figure 7B:
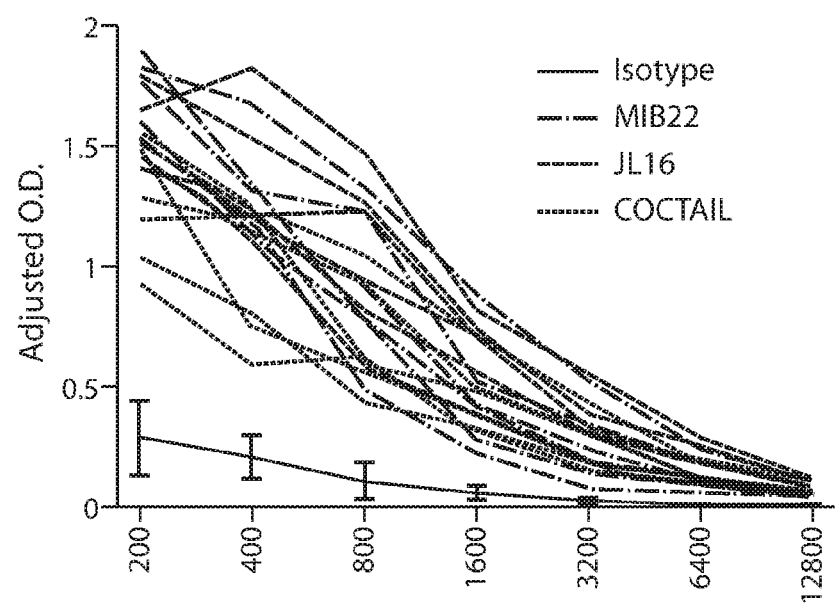
Figure 7C:
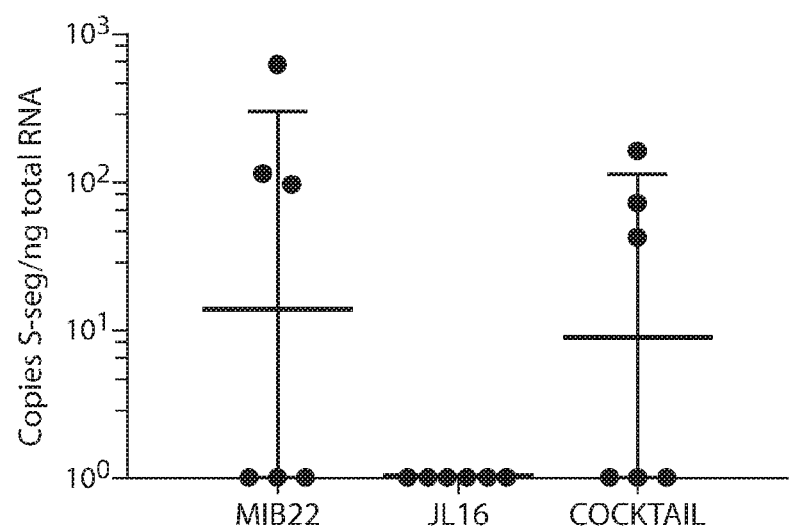

FIGS. 7A, 7B and 7C

These figures show the in-vivo efficacy of MIB22 and JL16 in protecting hamsters from a lethal challenge of ANDV infection. Twenty-four hamsters were inoculated with 200 foci-forming units (FFU) of ANDV. In FIG. 7A, groups of 6 hamsters were administered 50 mg/kg of one of MIB22, JL16, MIB22+JL16 cocktail or an isotype control at days 3 and 8 post-inoculation. Hamsters were monitored for disease. FIG. 7B shows ANDV-N ELISA from sera collected from survival hamster on 36 days post infection (DPI) for evidence of ANDV infection. In FIG. 7C, animals that survived to 36 DPI were euthanized and ANDV-specific S-segment RNA was quantified using qRT-PCR in the lungs tissue.

DETAILED DESCRIPTION OF THE INVENTION

Definitions

In this application, certain terms are used which shall have the meanings set forth as follows.

As used herein, "administer", with respect to an agent, means to deliver the agent to a subject's body via any known method. Specific modes of administration include, without limitation, intravenous, oral, sublingual, transdermal, subcutaneous, intraperitoneal and intrathecal administration. Preferred in this invention is intravenous administration.

In addition, in this invention, the various antibodies and other antigen-targeting agents used can be formulated using one or more routinely used pharmaceutically acceptable carriers. Such carriers are well known to those skilled in the art. For example, injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

"Andes Virus", as used herein, is exemplified by, but not limited to, hantavirus strain Chile-9717869 (Genbank No. AF291703.2). This term, as used herein, is also exemplified by, but not limited to, New World Hantaviruses (e.g., Sin Nombre, Choclo, Lechiguanas and Laguna Negra) and Old World Hantaviruses (e.g., Hantaan, Puumala and Dobrava-Belgrade).

As used herein, an "Andes Virus-binding domain" includes, without limitation, a domain that binds to a hantavirus glycoprotein, preferably to ANDV-GPC (Chile-9717869).

As used herein, the term "antibody" includes, without limitation, (a) an immunoglobulin molecule comprising two heavy chains (i.e., H chains, such as μ, δ, γ, α and ε) and two light chains (i.e., L chains, such as λ and κ) and which recognizes an antigen; (b) polyclonal and monoclonal immunoglobulin molecules; (c) monovalent and divalent fragments thereof, and (d) bi-specific forms thereof. Immunoglobulin molecules may derive from any of the commonly known classes, including but not limited to IgA, secretory IgA, IgG and IgM. IgG subclasses are also well known to those in the art and include, but are not limited to, human IgG1, IgG2, IgG3 and IgG4. Antibodies can be both naturally occurring and non-naturally occurring. Furthermore, antibodies include chimeric antibodies, wholly synthetic antibodies, single chain antibodies (e.g., scFv), and fragments thereof. Antibodies may contain, for example, all or a portion of a constant region (e.g., an Fc region) and a variable region, or contain only a variable region (responsible for antigen binding). Antibodies may be human, humanized or nonhuman. Methods for making antibodies, particularly monoclonal antibodies, are known (See, e.g., (25)). In particular, methods are known for making a monoclonal antibody or other recombinant protein that contains a predetermined variable region (See, e.g., (25)).

As used herein, a "dry component" of a pharmaceutically acceptable carrier may be, for example, one or more of an admixture of excipients such as sucrose, polysorbate, monobasic sodium phosphate (monohydrate), and dibasic sodium phosphate (dihydrate). A "liquid component" of a pharmaceutically acceptable carrier may be, for example, sterile water.

As used herein, an "effective amount" of the subject composition used in the subject prophylactic and therapeutic methods is an amount sufficient to deliver to the subject a prophylactic or therapeutic amount of the antibody or recombinant protein (collectively "active agent") therein, as appropriate. In one embodiment, an effective amount of the subject composition contains an amount of active agent (i.e., antibody or recombinant protein) sufficient to deliver from 0.1 mg/kg to 100 mg/kg of active agent to the subject (e.g., 0.1 mg/kg, 0.2 mg/kg, 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 20 mg/kg, 50 mg/kg, 75 mg/kg, 100 mg/kg, 125 mg/kg, 150 mg/kg, 175 mg/kg, 200 mg/kg, 50-100 mg/kg, 50-125 mg/kg, 50-150 mg/kg, 50-200 mg/kg, and 100-150 mg/kg).

Moreover, this dose can be administered once, or a plurality of times over the course of prophylaxis or therapy (e.g., once per week for three weeks, or twice with a period of from one to two days in between). In a preferred embodiment, a dose sufficient to deliver from 50-150 mg/kg (e.g., 125 mg/kg) of recombinant protein is administered twice, with a period of from one to two days between administrations.

As used herein, a subject who "has or may have recently been exposed to" Andes Virus includes, for example, a subject who experienced a high risk event (e.g., one in which he/she may have come into close contact with aerosols derived from the urine, feces or saliva of infected animals, or with infected human subjects) within the past month, three weeks, two weeks, one week, five days, four days, three days, two days or 24 hours.

As used herein, a "human antibody" is an antibody that occurs naturally in humans.

As used herein, a "human subject" can be of any age, gender or state of co-morbidity. In one embodiment, the subject is male, and in another, the subject is female.

The "IC50" value, with respect to antibody neutralization of Andes Virus, can be determined, for example, using the pseudovirus-based neutralization assay described herein, which assay employs ANDV-GPC (Chile-9717869).

As used herein, a subject is "infected" with Andes Virus if Andes Virus is present in the subject. Present in the subject includes, without limitation, present in at least some cells in the subject, and/or present in at least some extracellular fluid in the subject. In one embodiment, the Andes Virus present in the subject's cells is replicating. A subject who is exposed to Andes Virus may or may not become infected with Andres Virus.

As used herein, an "isolated" human antibody is a human antibody that is at least 90% pure (i.e., does not contain more than 10% protein impurity, whether or not that impurity is an antibody). Preferably, an isolated human antibody is at least 95%, 98%, 99% or 99.5% pure.

An antibody "neutralizes" a virus (e.g., Andes Virus) if it partly or fully impedes the virus' ability to infect a cell that, absent the antibody, it would otherwise infect.

As used herein, a "recombinant protein" means a protein that does not occur naturally.

As used herein, "reducing the likelihood" of a human subject's becoming symptomatic of an Andes Virus infection includes, without limitation, reducing such likelihood by at least 10%, at least 20%, at least 30%, at least 40%, at least 50%, at least 60%, at least 70%, at least 80%, at least 90%, or at least 95%. Preferably, reducing the likelihood of a human subject's becoming symptomatic of an Andes Virus infection means preventing the subject from becoming symptomatic of an Andes Virus infection.

As used herein, an event wherein a subject is "at risk of becoming exposed" to Andes Virus includes, without limitation, an event wherein the subject may come into close contact with aerosols derived from the urine, feces or saliva of infected animals, or with infected human subjects.

As used herein, the term "subject" includes, without limitation, a mammal such as a human, a non-human primate, a dog, a cat, a horse, a sheep, a goat, a cow, a rabbit, a pig, a hamster, a rat and a mouse. The subject methods are envisioned for these non-human embodiments, mutatis mutandis, as they are for human subjects in this invention.

As used herein, a human subject is "symptomatic" of an Andes Virus infection if the subject shows one or more symptoms known to appear in an Andes Virus-infected human subject after a suitable incubation period. Such symptoms include, without limitation, detectable Andes Virus in the subject, and those symptoms shown by patients afflicted with HCPS. HCPS-related symptoms include, without limitation, fever, chills, myalgia, cough, dyspnea, respiratory distress and cardiovascular collapse.

As used herein, "treating" a subject infected with Andes Virus and symptomatic of that infection includes, without limitation, (i) slowing, stopping or reversing the progression of one or more of the symptoms, (ii) slowing, stopping or reversing the progression of illness underlying such symptoms, (iii) reducing or eliminating the likelihood of the symptoms' recurrence, and/or (iv) slowing the progression of, lowering or eliminating the infection. In the preferred embodiment, treating a subject infected with Andes Virus and symptomatic of that infection includes (i) reversing the progression of one or more of the symptoms, (ii) reversing the progression of illness underlying such symptoms, (iii) preventing the symptoms' recurrence, and/or (iv) eliminating the infection. The progress of treating a subject infected with Andes Virus and symptomatic of that infection can be measured according to a number of clinical endpoints. These include, without limitation, lower or negative viral titer (also known as viral load) and the amelioration or elimination of one or more HCPS symptoms. In a preferred embodiment, the progress of treating a subject infected with Andes Virus and symptomatic of that infection can be measured by using RNA PCR to test for lower or negative viral titer in total lung tissue and/or sputum.

Embodiments of the Invention

In a study underlying this invention, two recombinant human monoclonal antibodies were developed using ANDV B cell clones from a convalescent patient with high titers of ANDV-neutralizing antibodies (P10). These two antibodies, MIB22 and JL16, bind ANDV glycoproteins (GPC) at a similar level as purified IgG isolated from P10 serum. Immunofluorescence was used to visually confirm binding to ANDV-GPC. Both monoclonal antibodies neutralize ANDV infection, and unexpectedly do so more potently than polyclonal IgG isolated from P10. However, MIB22 is 31-fold more potent at neutralizing ANDV infection than JL16, and 67-fold more potent than total polyclonal IgG isolated from P10. In contrast to polyclonal IgG serum from convalescent patients, the individual human monoclonal antibodies, MIB22 and JL16, are surprisingly effective tools for inhibiting and treating ANDV infection in humans.

Specifically, this invention provides a first isolated human antibody comprising two heavy chains and two light chains, (i) wherein each heavy chain comprises a variable region having the amino acid sequence shown in FIG. 1A, and each light chain comprises a variable region having the amino acid sequence shown in FIG. 1B, and (ii) wherein the antibody neutralizes Andes Virus with an IC50 of below 2.0 µg/ml. In one embodiment, the antibody neutralizes Andes Virus with an IC50 of below 1.0 µg/ml, 0.5 µg/ml or 0.2 µg/ml. In the preferred embodiment, the first antibody is the monoclonal antibody MIB22.

This invention also provides a first recombinant protein comprising an Andes Virus-binding domain that comprises two polypeptide regions, (i) wherein the first region has the amino acid sequence shown in FIG. 1A, and the second region has the amino acid sequence shown in FIG. 1B, and (ii) wherein the protein neutralizes Andes Virus with an IC50 of below 2.0 µg/ml. In one embodiment, the recombinant protein neutralizes Andes Virus with an IC50 of below 1.0 µg/ml, 0.5 µg/ml or 0.2 µg/ml. In another embodiment, the Andes Virus-binding domain comprises two polypeptide chains, wherein the first chain comprises a region having the amino acid sequence shown in FIG. 1A, and the second chain comprises a region having the amino acid sequence shown in FIG. 1B. In another embodiment, the Andes Virus-binding domain comprises one polypeptide chain (e.g., an scFv antibody).

Further, the first recombinant protein can comprise a single Andes Virus-binding domain (again, as with an scFv antibody), or two Andes Virus-binding domains (as with an IgG antibody).

In the preferred embodiment, the first recombinant protein is a monoclonal antibody.

This invention also provides a first composition comprising (i) the first antibody or the first recombinant protein, and (ii) a pharmaceutically acceptable carrier.

This invention provides a method for reducing the likelihood of a human subject's becoming symptomatic of an Andes Virus infection, wherein the subject is at risk of becoming exposed to Andes Virus, the method comprising administering to the subject an effective amount of the first composition. In one embodiment, the subject is at imminent risk of becoming exposed to Andes Virus (e.g., within one week, three days or 24 hours of a high risk event).

This invention also provides a method for reducing the likelihood of a human subject's becoming symptomatic of an Andes Virus infection, wherein the subject has or may have recently been exposed to Andes Virus, the method comprising administering to the subject an effective amount of the first composition.

This invention further provides a method for treating a human subject who is infected with Andes Virus and symptomatic of that infection, the method comprising administering to the subject an effective amount of the first composition.

This invention still further provides a kit comprising, in separate compartments, (i) a dry component of a pharmaceutically acceptable carrier admixed with the first antibody and/or with the first recombinant protein, and (ii) a liquid component of a pharmaceutically acceptable carrier. This kit permits reconstitution of lyophilized antibody and/or recombinant protein to form an injectable formulation immediately prior to administration.

This invention provides a second isolated human antibody comprising two heavy chains and two light chains, (i) wherein each heavy chain comprises a variable region having the amino acid sequence shown in FIG. 2A, and each light chain comprises a variable region having the amino acid sequence shown in FIG. 2B, and (ii) wherein the antibody neutralizes Andes Virus with an IC50 of below 10.0 µg/ml. In one embodiment, the antibody neutralizes Andes Virus with an IC50 of below 7.0 µg/ml (and in a further embodiment, below 6.0 µg/ml). In the preferred embodiment, the second antibody is the monoclonal antibody JL16.

This invention also provides a second recombinant protein comprising an Andes Virus-binding domain that comprises two polypeptide regions, (i) wherein the first region has the amino acid sequence shown in FIG. 2A, and the second region has the amino acid sequence shown in FIG. 2B, and (ii) wherein the protein neutralizes Andes Virus with an IC50 of below 10.0 µg/ml. In one embodiment, the Andes Virus-binding domain comprises two polypeptide chains, wherein the first chain comprises a region having the amino acid sequence shown in FIG. 2A, and the second chain comprises a region having the amino acid sequence shown in FIG. 2B. In another embodiment, the Andes Virus-binding domain comprises one polypeptide chain (e.g., an scFv antibody).

Further, the second recombinant protein can comprise a single Andes Virus-binding domain (again, as with an scFv antibody), or two Andes Virus-binding domains (as with an IgG antibody).

In the preferred embodiment, the second recombinant protein is a monoclonal antibody.

This invention also provides a second composition comprising (i) the second antibody or the second recombinant protein, and (ii) a pharmaceutically acceptable carrier.

This invention provides a method for reducing the likelihood of a human subject's becoming symptomatic of an Andes Virus infection, wherein the subject is at risk of becoming exposed to Andes Virus, the method comprising administering to the subject an effective amount of the second composition. In one embodiment, the subject is at imminent risk of becoming exposed to Andes Virus (e.g., within one week, three days or 24 hours of a high risk event).

This invention also provides a method for reducing the likelihood of a human subject's becoming symptomatic of an Andes Virus infection, wherein the subject has or may have recently been exposed to Andes Virus, the method comprising administering to the subject an effective amount of the second composition.

This invention further provides a method for treating a human subject who is infected with Andes Virus and symptomatic of that infection, the method comprising administering to the subject an effective amount of the second composition.

Finally, this invention provides a kit comprising, in separate compartments, (i) a dry component of a pharmaceutically acceptable carrier admixed with the second antibody and/or with the second recombinant protein, and (ii) a liquid component of a pharmaceutically acceptable carrier.

This invention will be better understood by reference to the examples which follow, but those skilled in the art will readily appreciate that the specific examples detailed are only illustrative of the invention as described more fully in the claims which follow thereafter.

Examples

A. Materials and Methods

Cell Lines and Viruses

HEK 293T cells (ATCC) were maintained in Dulbecco's Modified Eagle's Medium with NaHCO$_3$ and L-Glutamine, 10% heat-inactivated cosmic calf serum and 1× penicillin/streptomycin. HEK 293 cells were stably transduced with Integrin beta-3-expressing construct (NM_000212.2) (HEK 293-IB3). HEK 293-IB3 cells were maintained with the same media used for HEK 293T cells but supplemented with 500 µg/ml of G418. Peripheral blood mononuclear cells (PBMCs) were maintained in RPMI 1640 supplemented with NaHCO₃, L-Glutamine, 1×HEPES, 10% heat-inactivated fetal bovine serum and 1× penicillin/streptomycin.

Identification and Isolation of Human B Cells

Human samples were collected after signed informed consent in accordance with IRB-reviewed protocols by the participating institutions (hospitals) in Valdivia, Puerto Montt, Temuco cities. P10 was selected from a cohort of convalescent HCPS subjects previously infected with ANDV, who possessed high ANDV-neutralizing antibody titers. Peripheral blood mononuclear cells (PBMCs) and serum samples were collected from fresh blood using ethylenedi-aminetetraacetic acid-coated and serum Vacutainer tubes, respectively (BD). Serum samples were stored and frozen at −80° C. until analysis. PBMCs were isolated by Ficoll density gradient separation (Histopaque, Sigma-Aldrich) and stored in liquid nitrogen. To isolate antigen-specific B cells from P10, PBMCs were rested overnight and ANDV-specific memory B cells were labeled and sorted via flow cytometry.

Human Monoclonal Antibody Cloning, Expression and Sequence Analysis

Human antibody clones were generated by amplifying Ig genes from individual sorted B cells. Briefly, RNA from single cells was reverse transcribed. The cDNA was used to amplify IgH, Igλ or Igκ transcripts by two rounds of PCR. All PCR products were purified, sequenced and analyzed by ANARCI: antigen receptor numbering and receptor classification software (Oxford Protein Informatics Group, Oxford University, UK), IgBLAST/IMGT-V-Quest against the NCBI (National Center for Biotechnology Information, NIH) and the IMGT (The International Immunogenetics Information System) human variable gene databanks. Once analyzed, gene-specific primers containing restriction enzyme sites were used to amplify IgH, Igk, and Igl genes for cloning. Digested IgH, Igk, and Igλ PCR products were purified and directly cloned into pFUSEss-CHIg or pFUSEss-CLIg expression vectors (Invivogen Inc.). These expression constructs enable the expression of full-length human constant regions from IgG1, Igk or IgA. Briefly, PCR products were flanked with different restriction sites and ligated using a T4 DNA ligase (NEB, Inc). They were transformed into an *E. coli* DH5alpha strain (Invitrogen, Inc.). To verify the insertion colony, PCR and sequencing was performed. The positive clones were validated though sequencing and compared to original PCR sequences. Other molecular features of the heavy and light variable genes were collected from the sequence, such as junctional diversity, lengths, and somatic hypermutation rates and complementarity-determining regions (CDR).

Production and Purification of Human Monoclonal Antibodies

HEK 293 human embryonic kidney fibroblasts were cultured in Pro293 CD Serum-free Medium for 293 cells, with Pluronic, without L-glutamine and phenol red (Lonza). Once confluent, 293T cells were co-transfected with 7 ug of IgH and IgL chain-encoding plasmid DNA (pFUSEss-CHIg or pFUSEss-CLIg) with calcium phosphate. Transfection supernatants were collected five days post-transfection and purified with protein A/G Sepharose (GE Health). Purity was checked by SDS-PAGE.

Screening of Anti-GPC-ANDV Human Monoclonal Antibodies

Human monoclonal antibodies were screened using a flow cytometry-based binding assay. Briefly, 293T cells expressing surface glycoproteins from hantavirus strain Chile-9717869 were used to assess the binding of various dilutions and concentrations of human IgG or IgG-containing sera. Human sera or purified IgG were used for primary antibody staining, and Alexa fluor 488 anti-human IgG antibody was used as a secondary antibody. Binding was analyzed by flow cytometry and confocal microscopy.

Pseudovirus-Based Neutralization Assay of Anti-GPC-ANDV Human Monoclonal Antibody Viral particles pseudo-typed with Hantavirus Glycoproteins Gn and Gc (GPC) were produced by co-transfecting 293T cells with GPC expression construct encoding ANDV-GPC (Chile-9717869), along with the transfer vector pHR SIN CSGW and the packing vector psPAX2 to generate ANDV-GPC pseudo-typed lentiviral particles.

Supernatants containing pseudotyped ANDV particles were harvested 48 hours post-transfection and used to infect 293-IB3 cells (stable 293 cell line expressing the putative hantavirus receptor integrin b3). In samples for testing the neutralization capacity of IgG-containing sera or purified IgG, pseudovirus supernatant was pre-incubated with 1/50 to 1/20,000 dilutions of sera or with 0.1 µg/ml to 500 µg/ml of purified IgG prior to infection of 293-IB3 cells.

In Vivo Protective Efficacy of JL16 and MIB22 Human Monoclonal Antibodies after ANDV Lethal Challenge Twenty-four female Syrian hamsters (*Mesocricetus auratus*) (Harlan Labs), 5-6 weeks of age, were intranasally (IN) inoculated with 200 focus-forming units (FFU) of ANDV (Chile 9717869), diluted in 200 µL of sterile medium. Six hamsters were injected intraperitoneally (IP) at 3 and 8 days post-infection (DPI) with 50 mg/kg of one of isotype control antibody, JL16, MIB22, or a cocktail of JL16 and MIB22 (25 mg/kg each). Hamsters were monitored daily for disease signs. Survivors were euthanized at 36 DPI and sera and lung were collected for analysis.

B. Results

Isolation and Cloning of ANDV-Specific IgG CDR Sequences from Isolated B-Cell Clones Previous studies have shown that the passive transfer plasma from ANDV-convalescent patients to patients with acute ANDV hantavirus cardiopulmonary syndrome (HCPS) reduces symptoms and mortality (21, 22). These plasma donors were found to contain high titers of neutralizing antibodies directed against ANDV glycoproteins. Examined here is the binding and neutralizing capacity of monoclonal antibodies isolated from an ANDV-convalescent patient with high titers of ANDV-neutralizing antibodies (patient #10; P10).

Single cell ANDV-specific memory B cell clones were isolated from P10 through fluorescent labeling, followed by single cell sorting via flow cytometry. For each B cell clone, cDNA was generated by two-step reverse transcription (RT) using random primers. The variable heavy- and light-chain domains were then amplified by nested PCR. The first PCR used a primer mix that anneals to the V(D)J leader sequences and an immunoglobulin constant region reverse primer. The second PCR was performed with primers annealing to the 5' end of the variable (V) genes and an immunoglobulin nested constant region reverse primer. The PCR products were then purified and sequenced (29, 30).

Sequencing revealed the V(D)J composition of the variable antibody domains and the complementarity-determining regions (CDR). For this analysis, we used the ANARCI: antigen receptor numbering and receptor classification software (31, 32). This program curates nucleotide sequence information for immunoglubulins, T cell receptors, and Major Histocompatibility Complex (MHC) molecules. This program uniformly numbers IgG sequences based on the alignment of more than 5.000 sequences of IgG variable regions, taking into account structural data. Using these alignments, the framework regions (FR) and CDR regions were determined for two ANDV-specific B-cells for heavy and light chain sequences (FIGS. 1A, 1B, 2A and 2B).

Figure 4C:
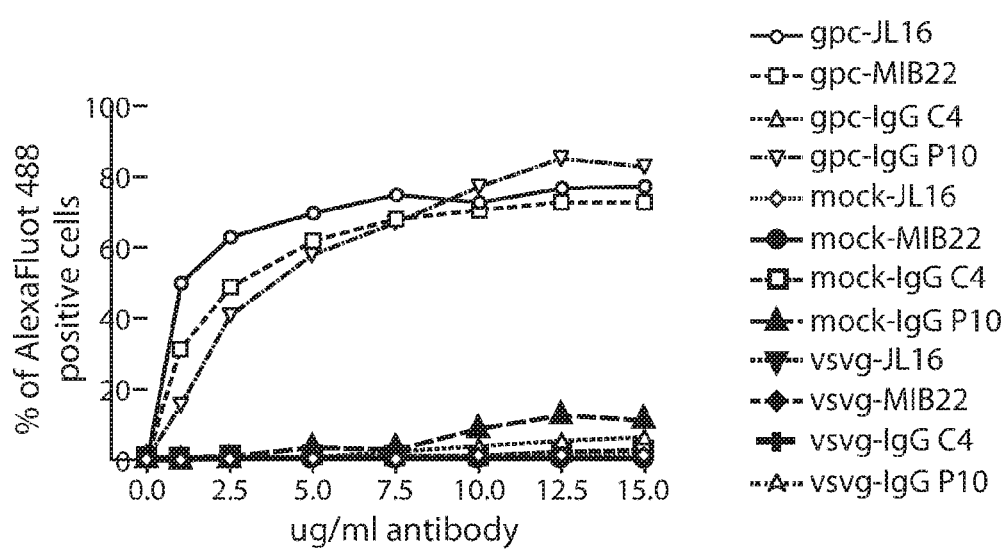
Figure 4D:
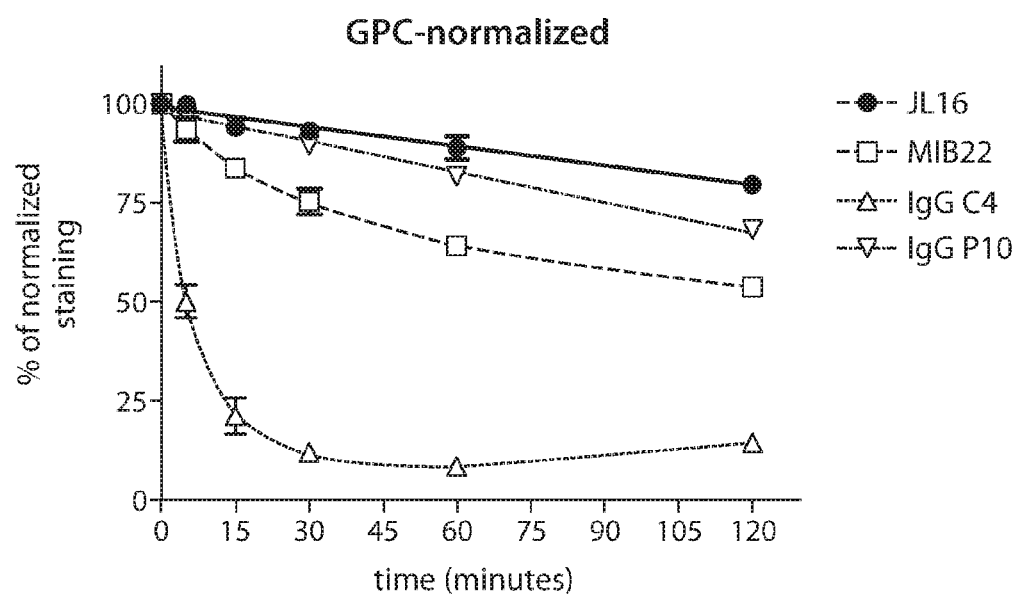

Sequence analysis revealed that MIB22 antibody displayed 86.46% of germline identity for the heavy chain and 92.71% of germline identity for the light chain. The MIB22 IgG heavy chain was identified as belonging to the IVH1-69 (FIG. 1C), with a top V gene match of HV1-69*13, HV1-69*01 or HV1-69D*01; with a top D gene match of HD3-10*02, HD1-7*01 or HD3-3*01 and a top J gene match of J5*02. The MIB22 IgG light chain was identified as belonging to the IGV2-14, with a top V gene match of LV2-14*03; and a top J gene match of LJ1*01.

On the other hand, sequence analysis revealed that JL16 antibody displayed 90.62% of germline identity for heavy chain and 95.83% of germline identity for light chains. The JL16 IgG heavy chain was identified as belonging to the IVHV3-74 (FIG. 2C), with a top V gene match of HV3-74*03; with a top D gene match of HD3-3*02, HD3-3*01; and a top J gene match of J3*01. The JL16 IgG light chain was identified as belonging to the IGV1-40, with a top V gene match of LV1-40*01 or LV1-40*02; and a top J gene match of LJ2*01 or LJ3*01.

Having confirmed that amplified sequences contained FR and CDR regions, these PCR products were cloned into IgG heavy and light chain expression vectors. These expression constructs enable the expression of full-length human heavy and light chain regions from IgG1, Igk or Igk

Measuring the Efficiency of ANDV-Specific IgG Antibody Production from 293T Cells To generate monoclonal antibodies, DNA vectors, encoding MIB22 or JL16, were co-transfected into 293T cells to generate IgG secreted into culture supernatants. Seventy-two hours post-transfection, 7 ml of supernatant were harvested and IgG was purified from 4 ml using protein A/G sepharose columns. IgG yields after column purification were measured by spectrophotometry at 560 nm using the BCA protein assay. A total of 9.36 mg and 9.614 mg were recovered from MIB22 and JL16, respectively. This translated into 2.34 and 2.53 mg/ml production efficiencies for MIB22 and JL16 in 293T cells, respectively (FIG. 3A).

To validate the purity of these isolates, the purified MIB22 and JL16 IgG preparations were run on an SDS denaturing gel. Robust bands were observed with a molecular weight of 55 KDa and 25 KDa for the heavy and light chain, respectively. Despite loading 15 μg of protein, Coomassie staining detected very low contamination in the purified samples. These purifications were thus used to conduct further antibody characterizations.

Examining the Level of ANDV Glycoprotein (GPC)-Specific Antibody Binding

To examine the level of antibody binding, the ability of MIB22 and JL16 IgG to bind to ANDV glycoproteins Gn and Gc was examined using a flow-cytometry based binding assay. First, 293T cells were transfected with an ANDV-GPC expression construct. After 48 hours post-transfection, ANDV-GPC or mock-transfected cells were incubated with total polyclonal IgG isolated from either an ANDV-naive donor (negative control) or the ANDV-convalescent patient used to isolated MIB22 and JL16 (P10; positive control). The levels of antibody binding to the surface of cells were then measured using flow cytometry. It was observed that IgG isolated from ANDV-naive donor did not bind to cells transfected with ANDV-GPC. In contrast, total IgG from P10 bound to 47.3% of ANDV-GPC-expressing cells (FIG. 4A).

Next examined was the ability of MIB22 and JL16 IgG to bind to un-transfected or ANDV-GPC-transfected cells. ANDV naive human monoclonal IgG was used as a negative control. Both MIB22 and JL16 were observed to bind to ANDV-GPC-expressing cells to a similar level, 55% and 50.5%, respectively (FIG. 4B; lower row). However, neither MIB22 nor JL16 binding to un-transfected 293T cells was observed (FIG. 4B; upper row). This demonstrates that binding was dependent on ANDV-GPC. Negative control IgG did not bind to either un-transfected or ANDV-GPC-expressing 293T cells.

To verify these results, the ability of different concentrations (1 to 15 μg/ml) of MIB22 and JL16 to bind to ANDV-GPC transfected cells was tested. As a control, un-transfected cells and cells transfected with VSV-G as non-ANDV-related envelope were used (FIG. 4C). Purified total IgG from patient 10 (P10) and purified total IgG from healthy donor (C4) were also used as controls. It was observed that P10 polyclonal IgG, JL16 and MIB22 specifically bound to cells expressing ANDV at all antibody concentrations used. In contrast, IgG isolated from ANDV-naive donor did not bind to ANDV-GPC-expressing cells or the mock-transfected control cells. At antibody concentrations of 10 μg/ml or higher, similar binding of all ANDV-specific antibodies was observed (FIG. 4C). However, in calculating the concentration at which 50% of ANDV-GPC is bound, it was observed that JL16 had a 50% binding concentration of 1.94 μg/ml versus 3.38 μg/ml for MIB22, and 3.51 μg/ml for purified P10 IgG. This suggests that JL16 may have a higher affinity for ANDV-GPC. No antibody binding to VSV-G or mock-transfected cells was observed.

Next, the relative affinities of these monoclonal antibodies were examined in comparison to P10 polyclonal IgG. For this, the dissociation rate of each antibody was measured using a flow cytometry-based method (33). In this experiment, 293T cells expressing ANDV-GPC were first incubated with a saturating amount of IgG and then incubated at 37° C. for various time periods. Surprisingly, while JL16 bound ANDV-GPC at a level similar to MIB22 and P10 polyclonal IgG, it dissociated at a much slower rate than both MIB22 and P10 polyclonal IgG. The proportion of bound JL16 after 120 minutes of incubation was 80% of saturating levels, representing a significantly higher proportion ($p=0.001$), as compared to MIB22 and P10 IgG, which displayed 54% and 68% of saturating levels, respectively (FIG. 4D). In contrast, the proportion of background binding with negative control IgG showed little change overtime. The kinetics of ANDV-GPC dissociation for JL16 was observed to be 0.17%/sec, compared to MIB22 and P10 polyclonal IgG which dissociated at a rate of 0.385 and 0.27%/sec, respectively. Together these results surprisingly suggest that JL16 has a higher relative affinity than either MIB22 or P10 polyclonal IgG.

Since MIB22 and JL16 bind to cells in an ANDV-GPC-dependent manner, it was next determined whether the antibodies could be used for immunofluorescence. 293 Ts cells were again transfected with ANDV glycoprotein expression vector and 48 hours post-transfection, cells were incubated with ANDV-negative IgG sera and MIB22. A staining profile was observed that is consistent with hantavirus envelope cluster on the surface of cells (FIG. 4E) (34). This demonstrated that the antibody not only could be used in flow cytometry, but also in immunofluorescence staining/imaging protocols.

Figure 5:
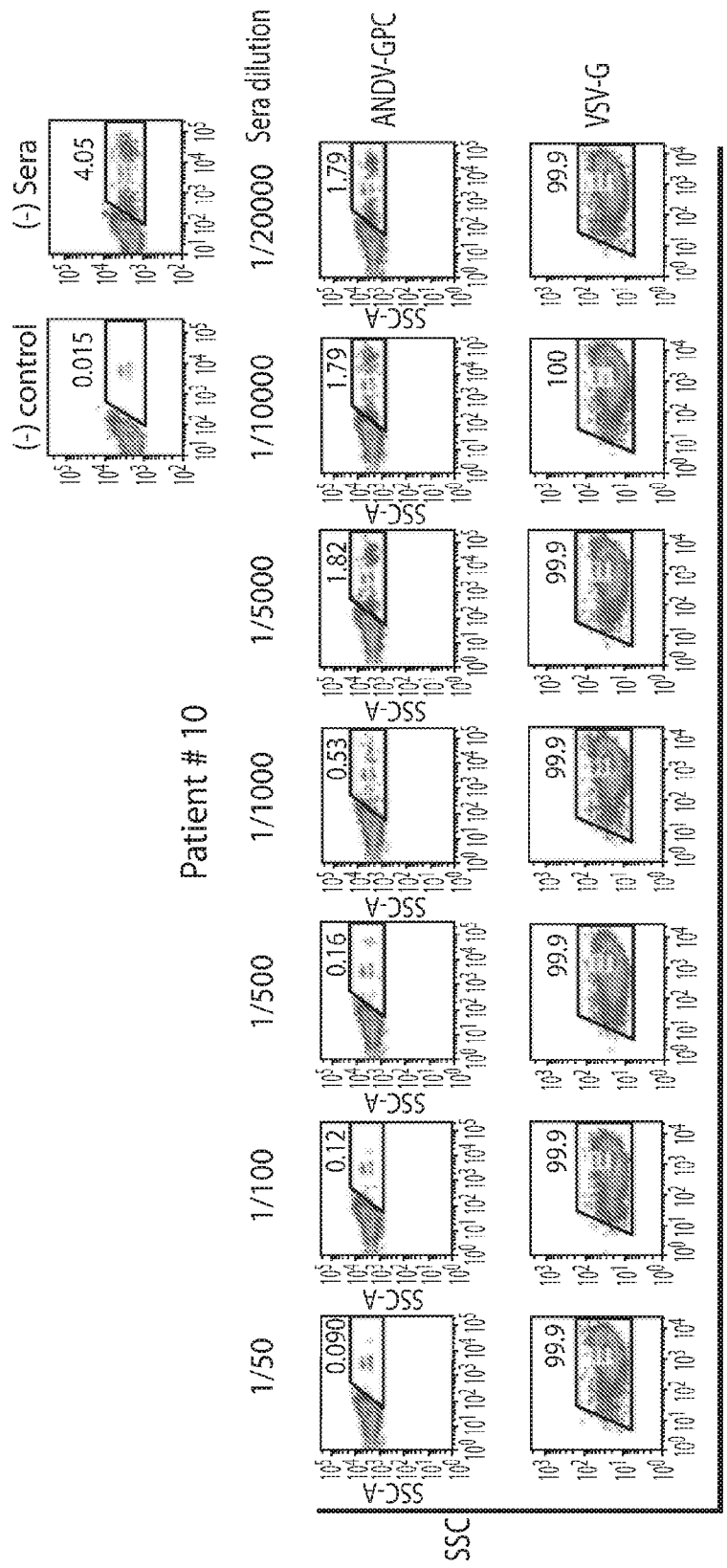

Comparing the In Vitro Neutralization Capacity of Novel ANDV-GPC-Binding Human Monoclonal Antibodies Virus particles pseudo-typed with ANDV-GPC were generated to examine the neutralization capacity of MIB22 and JL16. To control for neutralization specificity, viral particles pseudo-typed with a non-hantavirus related envelope, Vesicular Stomatitis Virus Glycoprotein (VSV-G) were used. First, viral input was normalized by quantifying HIV p24 core antigen by ELISA for both ANDV-GPC and VSV-G pseudo-typed particles. Particles were normalized using HIV core p24 ELISA assay. Next, HEK 293-IBT3 cells were infected with a standardized dose of pseudo-typed viral particles in the presence of serial dilutions of convalescent patient serum (P10). A potent dose-dependent inhibition of ANDV-GPC pseudo-typed particles was observed in the presence of increasing concentrations of P10 serum. Up to 98% inhibition of ANDV infection was observed at the highest concentration of serum tested (FIG. 5). In contrast, no inhibition of VSV-g infection was observed in the presence of P10 convalescent patient serum. This demonstrates the specificity of this ANDV infection neutralization assay.

Next, the neutralization capacity was examined for MIB22, JL16 and total IgG isolated from convalescent patient serum P10. First, ANDV-GPC pseudo-typed particles were pre-incubated with different dilutions of MIB22, JL16 or purified IgG (P10). It was observed that MIB22 antibody has a 31-fold higher neutralization capacity than JL16 antibody, with an IC50 of 0.2045 versus 6.6, respectively (FIG. 6B). MIB22 is also 67-fold more potent at ANDV neutralization than polyclonal IgG isolated from P10, the convalescent patient from whom MIB22 was cloned. In contrast, JL16 was 2.2-fold more potent at ANDV neutralization, as compared to polyclonal IgG from P10.

Examining the In Vivo Efficacy of MIB22 and JL16 Against a Lethal Dose of ANDV

To test the post-exposure efficacy of JL16 and MIB22 in vivo, the Syrian hamster model of ANDV disease was used. Upon productive infection, this model recapitulates many of the hallmarks of human ANDV-induced HCPS, including lethargy and pulmonary edema, and is nearly uniformly lethal (35, 36).

Four groups of six hamsters were challenged with 200 focus-forming units (FFU) of ANDV, and treated with 50 mg/kg of one of isotype control IgG, JL16, MIB22, or a combination of JL16 and MIB22 (25 mg/kg each) at 3 and 8 days post-infection (DPI) (FIG. 7A). All the hamsters given the control IgG succumbed to ANDV-induced HCPS within 15 days post-challenge (range of 10-15 days). No sign of disease was observed in either the group treated with JL16 or the group treated with the cocktail of both monoclonal antibodies. The hamsters in the group treated with MIB22 were reluctant to move during days 8 to 10. However, all of them survived and did not show any sign of disease after day 11.

At 36 days post-challenge, all surviving animals were considered to be convalescent and were euthanized. To confirm infection, an ANDV N-specific ELISA was performed and all euthanized animals had serum anti-N titers ≥12,800 (FIG. 7B). Next, the levels of residual ANDV in the lungs of the convalescent animals were assessed by quantifying the S-segment RNA using sensitive qRT-PCR. Low copy numbers of S-segment ANDV RNA were detected in 3 of 6 hamsters in each group that received either MIB22, or was given the cocktail therapy. The animals treated with JL16 showed no detectable ANDV RNA (FIG. 7C). The results of this experiment demonstrate that both MIB22 and JL16 are able to protect against ANDV post-exposure to lethal infection, with JL16 treatment leading to lower detectable residual viral loads, as compared to MIB22 treatment.

C. Discussion

Previous studies have shown that the passive transfusion of sera from ANDV-convalescent patients significantly lowers the morbidity and mortality from HCPS (21, 22). This study demonstrates that two monoclonal antibodies isolated from an ANDV-convalescent patient, characterized as a potent neutralizer, are themselves able to more potently neutralize ANDV infection in-vitro, as compared to the original donor serum (FIGS. 6A and 6B). Further, in examining the capacity of MIB22 and JL16 to inhibit ANDV infection in-vivo using a well-established model of ANDV-induced post-exposure prophylaxis, it was observed that both of these antibodies were able to protect animals from a lethal dose of ANDV-induced HCPS (FIGS. 7A-7C).

The variable regions of the heavy and light chains of two ANDV-specific human B cell clones from P10 were cloned into a human IgG1 backbone expression vector. Sequence analysis revealed that MIB22 antibody displayed 86.43% of germline identity for the heavy chain and 92.71% of germline identity for the light chain. On the other hand, JL16 antibody sequence analysis displayed a 90.62% of germline identity for the heavy chain and 95.83% of germline identity for the light chain. Analyses of germline gene usage and V(D)J recombination indicate that they originated from different B cell lineages.

Figure 3A:
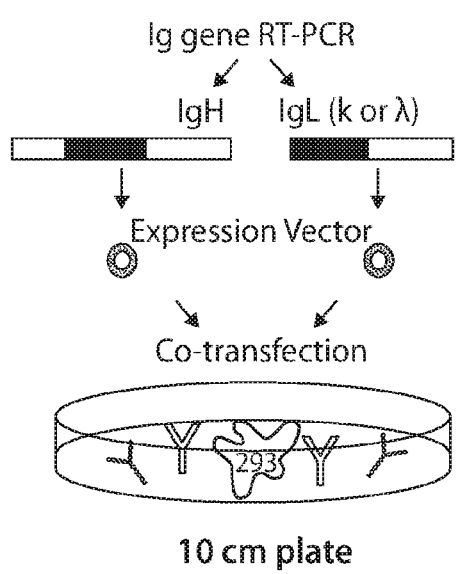
FIGS. 3A and 3B
Figure 3A:
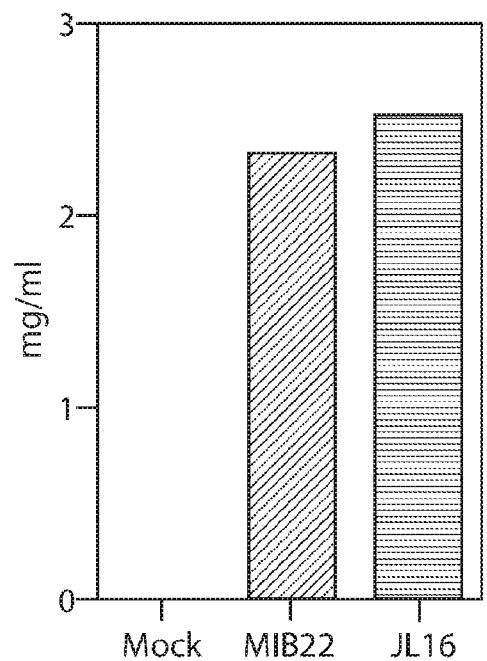
Figure 3B:
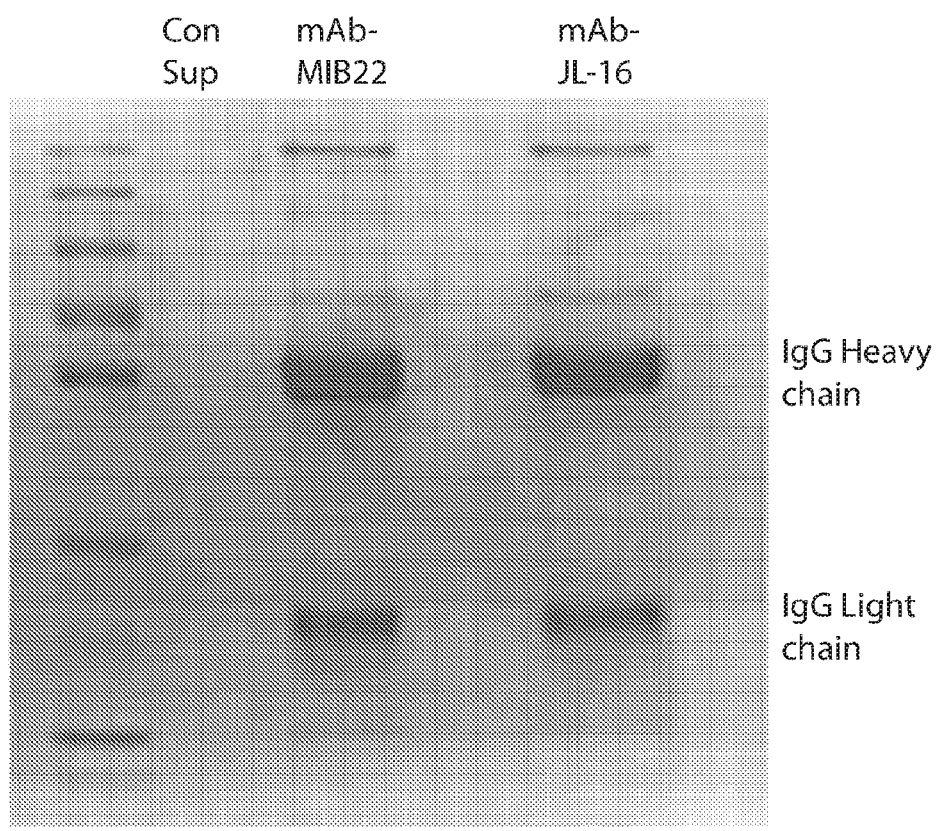

Transfection of the IgG1 expression constructs containing MIB22 heavy and lambda light chain sequences, and JL16 heavy and lambda light chain sequences, yielded efficient production of IgG antibodies in 293T culture supernatants (FIGS. 3A and 3B).

Analysis of purified IgG showed specific bands corresponding to IgG heavy and light chains, which confirms the functional expression/production of these two antibodies.

In addition, Coomassie staining reveled a high level of purity confirming that both antibody purifications could be used for further functional characterization.

In examining the binding of MIB22 and JL16 to ANDV-GPC, it was observed that both antibodies bound ANDV-GPC-expressing cells at a similar level (FIG. 4B). Moreover, MIB22 and JL16 did not bind to mock-transfected cells (GPC-negative). This demonstrates the specificity of MIB22 and JL16 binding to ANDV-GPC. Additionally, binding of ANDV-negative IgG to ANDV-GPC-expressing or mock-transfected cells (FIG. 4C) was not observed. Of note, JL16 bound to ANDV-GPC with a lower 50% ANDV-GPC-binding concentration as compared to MIB22 or P10 IgG. (FIG. 4C). In conjunction with antibody dissociation rate data (FIG. 4D), these data suggest that JL16 has a higher affinity for ANDV-GPC as compared to MIB22 or P10 polyclonal IgG.

Figure 4E:
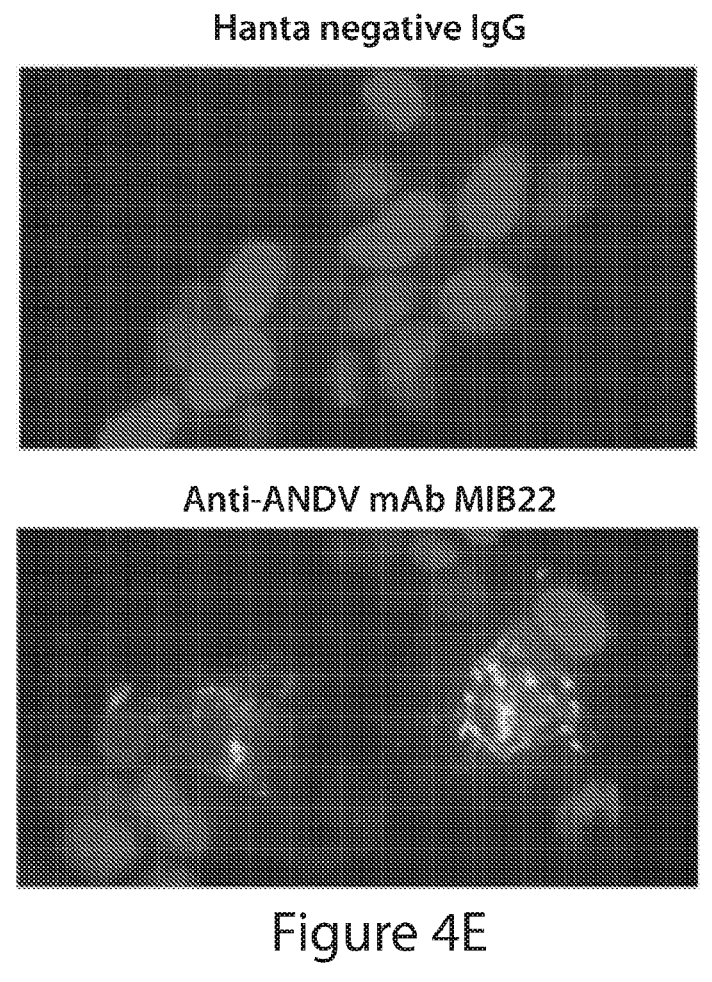

Further, immunofluorescence showed staining that suggests that the ANDV-GPC is localized in clusters on the surface of cells, as previously described for old world hantavirus (Yu et al.). It should be noted that since these antibodies are able to stain ANDV-GPC on live cells, this suggests that they bind exposed epitopes on the higher order structure of the ANDV-GPC (FIG. 4E).

Finally, in examining the capacity of MIB22 and JL16 to neutralize ANDV infection, it was observed that while MIB22 and JL16 possess a similar capacity to bind ANDV-GPC, MIB22 has a 31-fold higher neutralization capacity than does JL16 (IC50 0.2045 versus 6.6, respectively). Further, MIB22 has a 67-fold higher neutralization capacity than does polyclonal IgG isolated from the convalescent patient from which it was cloned. Therefore, MIB22 is distinguished by its potent capacity to neutralize ANDV infection, as compared to both total IgG isolated from P10, as well as another monoclonal antibody cloned from P10 (JL16) (despite all having similar levels of binding to ANDV-GPC).

Next, a well-characterized model of ANDV-induced HCPS was used to examine the in-vivo efficacy of MIB22 and JL16 (35-37). It was observed that both MIB22 and JL16 mediated 100% protection from a lethal challenge with ANDV (FIG. 7A). When the euthanized animals were examined for evidence of infection, all animals had seroconverted (FIG. 7B), indicating that infection was established prior to monoclonal antibody administration. Also examined was the viral copy number in the lungs of euthanized animals, the major site of viral replication and disease pathogenesis (39). It was observed that 50% of the MIB22- and cocktail-treated groups had low levels of detectable viral RNA, which is not surprising since viral RNAs have previously been shown to persist in tissue for several weeks, even in deceased animals (40). However, in the JL16-treated group, no detectable viral RNA was detected in the lungs of euthanized animals (FIG. 7C). These data show that JL16 is able to completely clear virus within this compartment despite having lower neutralization activity in vitro as compared to MIB22 (FIG. 6A). This suggests that JL16 is able to mediate other antibody-mediated antiviral responses (e.g., antibody-mediated cellular cytotoxicity, phagocytosis, and complement-mediated virolysis) (41). Altogether, these data demonstrate that the monoclonal antibodies JL16 and MIB22 are an effective treatment for HCPS.

REFERENCES

1. Hjelle, B. and Torres-Pérez, F., Hantaviruses in the Americas and their role as emerging pathogens. Viruses 2010 December; 2(12):2559-86.
2. Martinez-Valdebenito, C., et al., Person-to-person household and nosocomial transmission of Andes hantavirus, Southern Chile, 2011. Emerg. Infect. Dis. 2014; 20(10): 1629-36.
3. Martinez, V. P., et al., Person-to-person transmission of Andes virus. Emerg. Infect. Dis. 2005; 11(12):1848-53.
4. Padula, P. J., et al., Hantavirus pulmonary syndrome outbreak in Argentina: molecular evidence for person-to-person transmission of Andes virus. Virology 1998; 241 (2):323-30.
5. Wells, R. M., et al., Hantavirus transmission in the United States. Emerg. Infect. Dis. 1997; 3: 361-5.
6. Chilean Ministry of Health (MINSAL). Boletin Epidemiológico de Hantavirus Situación al 03 enero de 2014. Available online: http://epi.minsal.cl/epi/html/bolets/reportes/Hantavirus/hantavirus_2014.pdf.
7. Vaheri, A., et al., Uncovering the mysteries of hantavirus infections. Nat. Rev. Microbiol. 2013; 11(8):539-50.
8. Padula, P., et al., Transmission study of Andes hantavirus infection in wild sigmodontine rodents. J. Virol. 2004; 78:11972-9.
9. Schountz, T. and Prescott, J., Hantavirus Immunology of Rodent Reservoirs: Current Status and Future Directions. Viruses 2014; 6(3):1317-1335.
10. Vial, P. A., et al., Incubation period of hantavirus cardiopulmonary syndrome. Emerg. Infect. Dis. 2006; 12:1271-3.
11. Mertz, G. J., et al., Diagnosis and treatment of new world hantavirus infections. Curr. Opin. Infect. Dis. 2006; 19(5): 437-42.
12. Vial, P. A., et al., Hantavirus Study Group in Chile. High-dose intravenous methylprednisolone for hantavirus cardiopulmonary syndrome in Chile: a double-blind, randomized controlled clinical trial. Clin. Infect. Dis. 2013 October; 57(7):943-51.
13. MacNeil, A., et al., Sin Nombre virus-specific immunoglobulin M and G kinetics in hantavirus pulmonary syndrome and the role played by serologic responses in predicting disease outcome. J. Infect. Dis. 2010; 202:242-6.
14. Bharadwaj, M., et al., Humoral immune responses in the hantavirus cardiopulmonary syndrome. J. Infect. Dis. 2000; 182(1):43-8.
15. Ye, C., et al., Neutralizing antibodies and Sin Nombre virus RNA after recovery from hantavirus cardiopulmonary syndrome. Emerg. Infect. Dis. 2004; 10(3):478-82.
16. Custer, D. M., et al., Active and passive vaccination against hantavirus pulmonary syndrome with Andes virus M genome segment-based DNA vaccine. J. Virol. 2003; 77(18):9894-905.
17. Hooper, J. W., et al., Immune serum produced by DNA vaccination protects hamsters against lethal respiratory challenge with Andes virus. J. Virol. 2008; 82(3):1332-8.
18. Brocato, R., et al., DNA vaccine-generated duck polyclonal antibodies as a postexposure prophylactic to prevent hantavirus pulmonary syndrome (HPS). PLoS One 2012; 7:e35996.
19. Hooper, J. W., et al., DNA vaccine-derived human IgG produced in transchromosomal bovines protect in lethal models of hantavirus pulmonary syndrome. Sci. Transl. Med. 2014; 6(264):264ra162.
20. Haese, N., et al., Antiviral Biologic Produced in DNA Vaccine/Goose Platform Protects Hamsters Against Hantavirus Pulmonary Syndrome When Administered Postexposure. PLoS Negl. Trop. Dis. 2015; 9(6):e0003803.
21. Vial, P. A., et al., Hantavirus Study Group in Chile. A non-randomized multicentre trial of human immune plasma for treatment of hantavirus cardiopulmonary syndrome caused by Andes virus. Antivir. Ther. 2015; 20(4): 377-86.

22. Dolgin, E., Hantavirus treatments advance amidst outbreak in US park. Nat. Med. 2012; 18(10):1448.
23. Enria, D. A., et al., Importance of dose of neutralising antibodies in treatment of Argentine haemorrhagic fever with immune plasma. Lancet 1984; 2(8397):255-6.
24. Casadevall, A., et al., Passive antibody therapy for infectious diseases. Nat. Rev. Microbiol. 2004; 2(9):695-703.
25. Wilson, P. C. and Andrews, S. F., Tools to therapeutically harness the human antibody response. Nat. Rev. Immunol. 2012; 12:709-19.
26. Scheid, J. F., et al., Broad diversity of neutralizing antibodies isolated from memory B cells in HIV-infected individuals. Nature 2009; 458:636-40.
27. Mouquet, H., et al., Memory B cell antibodies to HIV-1 gp140 cloned from individuals infected with clade A and B viruses. PLoS One 2011; 6:e24078.
28. Wu, X., et al., Rational design of envelope identifies broadly neutralizing human monoclonal antibodies to HIV-1. Science 2010; 329:856-61.
29. Tiller, T., et al., Efficient generation of monoclonal antibodies from single human B cells by single cell RT-PCR and expression vector cloning. J. Immunol. Methods 2008; 329(1-2):112-24.
30. Smith, K., et al., Rapid generation of fully human monoclonal antibodies specific to a vaccinating antigen. Nat. Protoc. 2009; 4(3):372-84.
31. Dunbar, J., and Deane, C. M., ANARCI: antigen receptor numbering and receptor classification, Bioinformatics, Volume 32, Issue 2, 15 Jan. 2016, Pages 298-300, https://doi.org/10.1093/bioinformatics/btv552.
32. Abhinandan, K. R., and Martin, A. C. R., Analysis and improvements to Kabat and structurally correct numbering of antibody variable domains. 2008 Mol. Immunol., 45:3832-3839.
33. Geuijen, C. A., et al., Affinity ranking of antibodies using flow cytometry: application in antibody phage display-based target discovery. Journal of Immunological Methods 2005; (302):68-77.
34. Yu, L., et al., A recombinant pseudotyped lentivirus expressing the envelope glycoprotein of hantaan virus induced protective immunity in mice. Virol. J. 2013 Oct. 5; 10:301.
35. Hooper, J. W., et al., A lethal disease model for hantavirus pulmonary syndrome. Virol. 2001; (289):6-14.
36. Martinez, V. P. and Padula, P. J., Induction of protective immunity in a Syrian hamster model against a cytopathogenic strain of Andes virus. J. Med. Virol. 2012; (84):87-95.
37. Safronetz, D., et al., Pathogenesis and host response in Syrian hamster following intranasal infection with Andes virus. PLoS Pathog., 2011 December; 7(12):e1002426.
38. Howell, K. A., et al., Antibody Treatment of Ebola and Sudan Virus Infection via a Uniquely Exposed Epitope within the Glycoprotein Receptor-Binding Site. Cell Rep. 2016; 17; 15(7):1514-26.
39. Corti, D., et al., Protective monotherapy against lethal Ebola virus infection by a potently neutralizing antibody. Science. 2016; 18; 351(6279):1339-42.
40. Prescott, J., et al., Postmortem stability of Ebola virus, Emerg. Infect. Dis. 2015 May; 21(5):856-9.
41. Marasco, W. A. and Sui, J., The growth and potential of human antiviral monoclonal antibody therapeutics, Nat. Biotechnol. 2007 December; 25(12):1421-34.

What is claimed is:

1. A method for reducing the likelihood of a human subject's becoming symptomatic of an Andes Virus infection, wherein the subject is at risk of becoming exposed to Andes Virus, the method comprising intravenously administering to the subject an effective amount of a composition comprising (a) a pharmaceutically acceptable carrier and (b) a human antibody comprising two heavy chains and two light chains, (i) wherein each heavy chain comprises a variable region having the amino acid sequence set forth in SEQ ID NO:2, and each light chain comprises a variable region having the amino acid sequence set forth in SEQ ID NO:4, and (ii) wherein the antibody neutralizes Andes Virus with an $IC_{50}$ of below 2.0 µg/ml.

2. The method of claim 1, wherein the antibody is the monoclonal antibody MIB22.

3. The method of claim 1, wherein the antibody is administered twice with a period of from one to two days between administrations, and wherein each administration is sufficient to deliver 50-150 mg/kg of the antibody to the subject.

4. A method for reducing the likelihood of a human subject's becoming symptomatic of an Andes Virus infection, wherein the subject is at risk of becoming exposed to Andes Virus, the method comprising intravenously administering to the subject an effective amount of a composition comprising (a) a pharmaceutically acceptable carrier and (b) a recombinant protein comprising an Andes Virus-binding domain that comprises two polypeptide chains, (i) wherein the first chain comprises a region having the amino acid sequence set forth in SEQ ID NO:2, and the second chain comprises a region having the amino acid sequence set forth in SEQ ID NO:4, and (ii) wherein the protein neutralizes Andes Virus with an $IC_{50}$ of below 2.0 µg/ml.

5. The method of claim 4, wherein the recombinant protein comprises two Andes Virus-binding domains.

6. The method of claim 4, wherein the recombinant protein is a monoclonal antibody.

7. The method of claim 4, wherein the recombinant protein is administered twice with a period of from one to two days between administrations, and wherein each administration is sufficient to deliver 50-150 mg/kg of the recombinant protein to the subject.

8. A method for reducing the likelihood of a human subject's becoming symptomatic of an Andes Virus infection, wherein the subject has or may have recently been exposed to Andes Virus, the method comprising intravenously administering to the subject an effective amount of a composition comprising (a) a pharmaceutically acceptable carrier and (b) a human antibody comprising two heavy chains and two light chains, (i) wherein each heavy chain comprises a variable region having the amino acid sequence set forth in SEQ ID NO:2, and each light chain comprises a variable region having the amino acid sequence set forth in SEQ ID NO:4, and (ii) wherein the antibody neutralizes Andes Virus with an $IC_{50}$ of below 2.0 µg/ml.

9. The method of claim 8, wherein the antibody is the monoclonal antibody MIB22.

10. The method of claim 8, wherein the antibody is administered twice with a period of from one to two days between administrations, and wherein each administration is sufficient to deliver 50-150 mg/kg of the antibody to the subject.

11. A method for reducing the likelihood of a human subject's becoming symptomatic of an Andes Virus infection, wherein the subject has or may have recently been exposed to Andes Virus, the method comprising intravenously administering to the subject an effective amount of a composition comprising (a) a pharmaceutically acceptable carrier and (b) a recombinant protein comprising an Andes Virus-binding domain that comprises two polypeptide chains, (i) wherein the first chain comprises a region having the amino acid sequence set forth in SEQ ID NO:2, and the second chain comprises a region having the amino acid sequence set forth in SEQ ID NO:4, and (ii) wherein the protein neutralizes Andes Virus with an $IC_{50}$ of below 2.0 µg/ml.

12. The method of claim 11, wherein the recombinant protein comprises two Andes Virus-binding domains.

13. The method of claim 11, wherein the recombinant protein is a monoclonal antibody.

14. The method of claim 11, wherein the recombinant protein is administered twice with a period of from one to two days between administrations, and wherein each administration is sufficient to deliver 50-150 mg/kg of the recombinant protein to the subject.

15. A method for treating a human subject who is infected with Andes Virus and symptomatic of that infection, the method comprising intravenously administering to the subject an effective amount of a composition comprising (a) a pharmaceutically acceptable carrier and (b) a human antibody comprising two heavy chains and two light chains, (i) wherein each heavy chain comprises a variable region having the amino acid sequence set forth in SEQ ID NO:2, and each light chain comprises a variable region having the amino acid sequence set forth in SEQ ID NO:4 and (ii) wherein the antibody neutralizes Andes Virus with an $IC_{50}$ of below 2.0 µg/ml.

16. The method of claim 15, wherein the antibody is the monoclonal antibody MIB22.

17. The method of claim 15, wherein the antibody is administered twice with a period of from one to two days between administrations, and wherein each administration is sufficient to deliver 50-150 mg/kg of the antibody to the subject.

18. A method for treating a human subject who is infected with Andes Virus and symptomatic of that infection, the method comprising intravenously administering to the subject an effective amount of a composition comprising (a) a pharmaceutically acceptable carrier and (b) a recombinant protein comprising an Andes Virus-binding domain that comprises two polypeptide chains, (i) wherein the first chain comprises a region having the amino acid sequence set forth in SEQ ID NO:2, and the second chain comprises a region having the amino acid sequence set forth in SEQ ID NO:4, and (ii) wherein the protein neutralizes Andes Virus with an $IC_{50}$ of below 2.0 µg/ml.

19. The method of claim 18, wherein the recombinant protein comprises two Andes Virus-binding domains.

20. The method of claim 18, wherein the recombinant protein is a monoclonal antibody.

21. The method of claim 18, wherein the recombinant protein is administered twice with a period of from one to two days between administrations, and wherein each administration is sufficient to deliver 50-150 mg/kg of the recombinant protein to the subject.

* * * * *